US010694996B2

(12) United States Patent
Williamson et al.

(10) Patent No.: US 10,694,996 B2
(45) Date of Patent: Jun. 30, 2020

(54) INSTRUMENTED PHYSIOTHERAPEUTIC, AMBULATORY, AND MOBILITY VEST TO MONITOR AND PROVIDE FEEDBACK TO PATIENTS AND CAREGIVERS

(71) Applicant: Abililife, Inc., Pittsburgh, PA (US)

(72) Inventors: Courtney Denise Williamson, Pittsburgh, PA (US); Britta Kathleen Ulm, Pittsburgh, PA (US); Noah Peter Papas, Pittsburgh, PA (US)

(73) Assignee: Abililife, Inc., Pittsburgh, PA (US)

( * ) Notice: Subject to any disclaimer, the term of this patent is extended or adjusted under 35 U.S.C. 154(b) by 0 days.

(21) Appl. No.: 15/840,675

(22) Filed: Dec. 13, 2017

(65) Prior Publication Data
US 2018/0098732 A1    Apr. 12, 2018

Related U.S. Application Data

(63) Continuation of application No. PCT/US2016/037424, filed on Jun. 14, 2016, which
(Continued)

(51) Int. Cl.
*A61F 5/00* (2006.01)
*A61B 5/00* (2006.01)
(Continued)

(52) U.S. Cl.
CPC .......... *A61B 5/6805* (2013.01); *A61B 5/0022* (2013.01); *A61B 5/02055* (2013.01);
(Continued)

(58) Field of Classification Search
USPC ......................................................... 602/19
See application file for complete search history.

(56) References Cited

U.S. PATENT DOCUMENTS 7,842,000 B2 * 11/2010 Lai .......................... A61F 5/026
602/19
8,945,328 B2 * 2/2015 Longinotti-Buitoni ......................
A61B 5/0002
156/234
(Continued)

FOREIGN PATENT DOCUMENTS

WO    2016205235 A1    12/2016

OTHER PUBLICATIONS

PCT/US2016/037424, "International Application Serial No. PCT/US2016/037424, International Preliminary Report on Patentability dated Dec. 28, 2017", AbiliLife, Inc., 7 Pages.
(Continued)

*Primary Examiner* — Kim M Lewis
(74) *Attorney, Agent, or Firm* — GTC Law Group PC & Affiliates

(57) ABSTRACT

Improved methods and systems are disclosed for a physiotherapeutic device having a waist tensioning system and a spine support system that may enable correction and/or maintaining of postural stance for individuals suffering from poor posture and/or neurodegenerative disease. The physiotherapeutic device includes a tensioner mechanism. Waist straps attached to the lumbar expansion portion may be configured to be routed through the anchor and wrapped around the vest when the user wears the device. The device also includes shoulder straps, each having a first end attached to a top, rear portion of the vest and a second end attached to the central member. The physiotherapeutic device may be outfitted with sensors to detect statuses and symptoms relevant to the patient and caregiver and to provide reporting and feedback to both the patient and caregiver.

12 Claims, 13 Drawing Sheets

Related U.S. Application Data is a continuation-in-part of application No. 14/728,138, filed on Jun. 2, 2015, now Pat. No. 9,931,236.

(60) Provisional application No. 62/311,256, filed on Mar. 21, 2016, provisional application No. 62/175,778, filed on Jun. 15, 2015, provisional application No. 62/049,671, filed on Sep. 12, 2014.

(51) Int. Cl.
| | |
|---|---|
| *A61B 5/11* | (2006.01) |
| *A61F 5/02* | (2006.01) |
| *A61B 7/04* | (2006.01) |
| *A61B 5/0295* | (2006.01) |
| *A61B 5/16* | (2006.01) |
| *A61B 5/08* | (2006.01) |
| *A61B 5/024* | (2006.01) |
| *A61B 5/0205* | (2006.01) |

(52) U.S. Cl.
CPC ........ *A61B 5/0295* (2013.01); *A61B 5/02438* (2013.01); *A61B 5/0816* (2013.01); *A61B 5/1117* (2013.01); *A61B 5/1118* (2013.01); *A61B 5/165* (2013.01); *A61B 5/4082* (2013.01); *A61B 5/486* (2013.01); *A61B 5/4833* (2013.01); *A61B 5/4836* (2013.01); *A61B 5/7282* (2013.01); *A61B 5/746* (2013.01); *A61B 5/747* (2013.01); *A61B 7/04* (2013.01); *A61F 5/026* (2013.01); *A61F 5/028* (2013.01); *A61B 5/1116* (2013.01); *A61B 2560/0475* (2013.01); *A61B 2562/0219* (2013.01); *A61B 2562/0223* (2013.01)

(56) References Cited

U.S. PATENT DOCUMENTS

| | | | |
|---|---|---|---|
| 9,125,442 B2* | 9/2015 | Brown | A61F 5/026 |
| 9,456,919 B2* | 10/2016 | Pollack | A61F 5/026 |
| 9,931,236 B2 | 4/2018 | Williamson et al. | |
| 2005/0070830 A1* | 3/2005 | Schultz | A61B 5/1116 602/19 |
| 2008/0162088 A1 | 7/2008 | Devaul et al. | |
| 2009/0234262 A1 | 9/2009 | Reid et al. | |
| 2012/0139731 A1 | 6/2012 | Razoumov et al. | |
| 2012/0197160 A1 | 8/2012 | Reinhardt et al. | |
| 2013/0345612 A1* | 12/2013 | Bannister | A61B 5/1116 602/19 |
| 2014/0180171 A1 | 6/2014 | Hyde et al. | |
| 2014/0364784 A1* | 12/2014 | Hyde | A61F 5/028 602/19 |

OTHER PUBLICATIONS

PCT/US2016/037424, "International Application Serial No. PCT/US2016/037424, International Search Report and Written Opinion dated Sep. 1, 2016", AbiliLife, Inc., 11 pages.

* cited by examiner

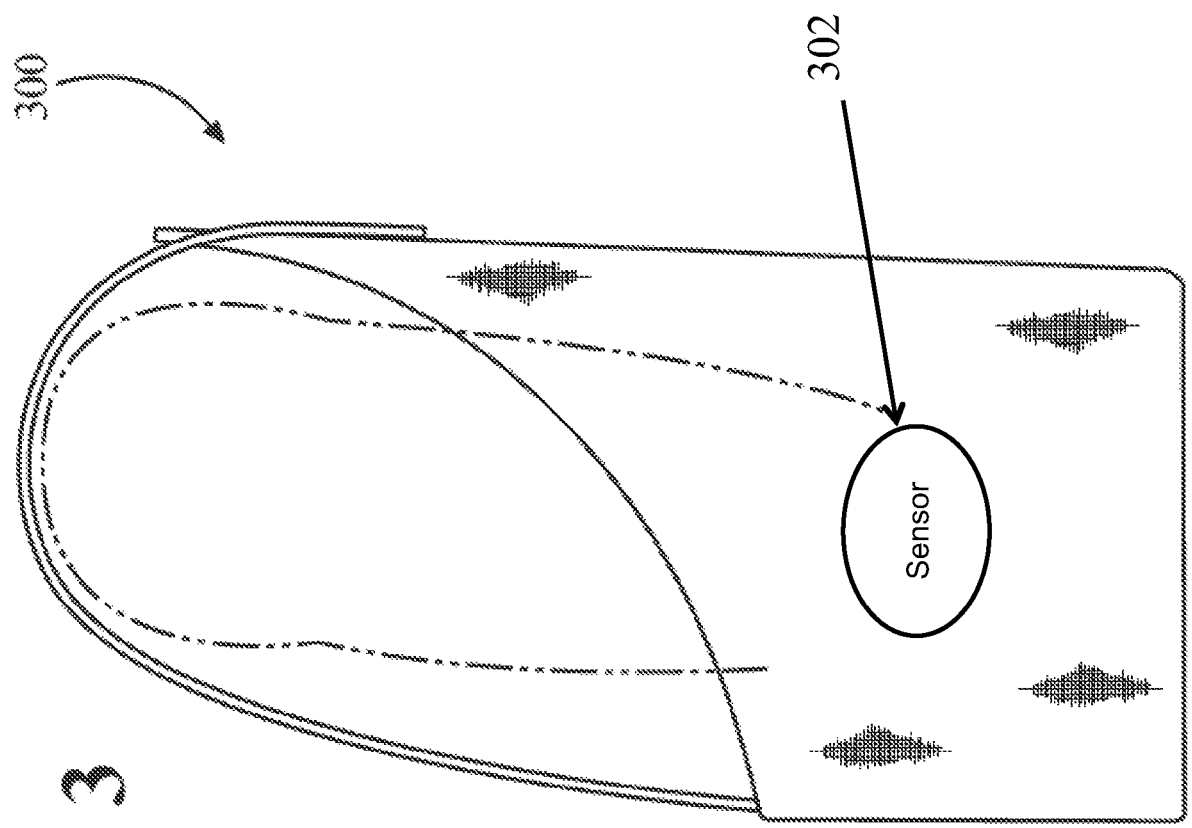

INSTRUMENTED PHYSIOTHERAPEUTIC, AMBULATORY, AND MOBILITY VEST TO MONITOR AND PROVIDE FEEDBACK TO PATIENTS AND CAREGIVERS

CLAIM TO PRIORITY

This application is a continuation of international application no. PCT/US2016/037424, filed Jun. 14, 2016.

Application PCT/US2016/037,424 is a continuation-in-part of U.S. patent application Ser. No. 14/728,138, filed on 2 Jun. 2015 (0085022-000003); and PCT/US2016/037,424 claims priority to U.S. provisional application 62/175,778 filed 15 Jun. 2015 and U.S. provisional application 62/311, 256, filed on 21 Mar. 2016.

U.S. patent application Ser. No. 14/728,138 claims priority to U.S. Provisional application 62/049,671, filed 12 Sept 2014 (0085022-000002).

Each of the foregoing applications is incorporated by reference herein in the entirety for all purposes.

STATEMENT REGARDING GOVERNMENT FUNDING

This application may be subject to government funding awarded on Jan. 1, 2016 by the National Science Foundation, Grant No. 1549761.

BACKGROUND

Field

The present disclosure relates generally to a physiotherapeutic device, and in particular to an instrumented vest to assist individuals having ambulatory and other mobility disabilities, including problems related to posture, and to detect and report statuses relevant to patient and caregiver.

Description of the Related Art

Persons with Parkinson's disease, multiple sclerosis, amyotrophic lateral sclerosis, spinal deformities (e.g., kyphosis), and/or other neurodegenerative diseases often experience issues with muscle rigidity, as well as problems with their posture and balance. At later stages of Parkinson's disease 90% of patients suffer from postural instability. Parkinson's disease is a chronic and progressive movement disorder that involves the malfunction and/or death of vital nerve cells in the brain, called neurons. Some neurons produce the chemical dopamine, a chemical that sends messages to the part of the brain that controls movement and coordination. As Parkinson's progresses, the amount of dopamine produced in the brain decreases due to the death of neurons, leaving a person unable to control movement normally. This leads to the development of tremors, bradykinesia, rigidity or postural instability. A diagnosis of Parkinson's requires the presence of at least two of these primary motor symptoms, one of which must be tremor or bradykinesia.

Parkinson's disease affects one and a half million individuals in the United States with about 50,000 newly diagnosed each year. Most of the disability caused by Parkinson's disease relates to symptoms such as gait dysfunction, loss of balance, swallowing and speech difficulties, autonomic disturbances and cognitive decline, which are less influenced by available therapies.

The plethora of symptoms exhibited by Parkinson's patients has led to numerous scientific studies and many using machine learning. Several individuals have worked to more accurately and quickly diagnose Parkinson's disease. Shianghau Wu, Jiannjong Guo used audio recordings to determine early signals in an individual's voice that can lead to a diagnosis of Parkinson's. While others used a test battery for assessing patient state in advanced Parkinson's disease, consisting of self-assessments and motor tests, constructed and implemented on a hand computer with touch screen.

Recently wearable sensors have been used to track Parkinson's symptoms. Such work has included the use of accelerometers of smartphones to detect Parkinson's symptoms, such as resting tremor and bradykinesia. Accelerometers have been used in an uncontrolled home environment to automatically detect Parkinson's disease motor symptoms in daily living environments. Researchers were able to detect specific symptoms (e.g. dyskinesia) which conformed to a daily log maintained by the patients. There has also been research on measurement of motor symptoms in Parkinson's disease with full-body motion capture data and personalized Parkinson's disease interventions using data from a smartphone and a smartwatch. Still other research has been done to characterize the postural behavior of early mild Parkinson's disease patients using accelerometers placed on an individual's back. All of the previous work performed by these groups demonstrates a correlation to be found between wearable sensor data and Parkinson's symptoms.

As mentioned above, Parkinson's disease patients require postural support. One form of providing support and maintaining proper posture is through a brace or a vest, such as a gait vest. Some existing back braces consist of an elongated triangular configuration for the spine system, along with adjustable shoulder straps mounted onto a lightweight waist support to allegedly assist with posture by providing a compressive force to the wearer's lower waist area. Other existing brace devices use a waist cord that can be pulled about the wearer's waist to adjust tensioning of the wearer's upper back and shoulders. Some braces provide straightening forces in the mid-torso section rather than at the shoulder.

While current devices provide a means to force an individual to exhibit proper posture, there is a need for devices that provide support and proper force vector tensioning to assist a user to maintain balance and posture while performing daily activities and functions. Moreover, current devices fail to offer a system allowing proper range of motion due to the rigidity and awkwardness of the devices. Furthermore, such devices provide crude and unsophisticated means of correcting posture that may even cause additional harm. In addition to postural support, patients and caregivers would benefit from robust techniques to identify, diagnose, and quantify symptoms and statuses experienced by Parkinson's patients. Such benefit would be enhanced if it were combined with postural support methods and systems.

SUMMARY

A physiotherapeutic device has a waist tensioning system and a spine support system that may enable correction and/or maintaining of postural stance for individuals suffering from poor posture and/or neurodegenerative disease.

The device is a garment that includes a waist tensioner mechanism and a spine support system. While the device is described and depicted as a vest, one skilled in the art will appreciate, with the benefit of the present disclosure, that the device may be configured for use as any type of garment. This may include, but is not limited to, a shirt, jacket, jumpsuit, or other clothing article.

The vest includes a back portion and two front panels, wherein the back portion has a cervical expansion portion and a lumbar extension portion. The vest may include a plurality of segment panels, each exhibiting an elasticity so as to provide support and therapeutic effect. A support member pouch may be disposed on the back portion, which is configured to retain a support member in alignment with a user's spine when donning the vest. Included on a bottom portion of the vest may be a central fastener, which is configured to retain the support member within the support member pouch by covering and concealing an opening leading into the support member pouch.

A tensioner mechanism, including a central member may extend from the cervical expansion portion, where an anchor is in mechanical connection therewith. Waist straps attached to the lumbar expansion portion may be configured to be routed through the anchor and wrapped around the vest when the user dons the device. The vest also includes shoulder straps, each having a first end attached to a top, rear portion of the vest and a second end attached to the central member.

The vest may include fasteners disposed on a surface of each front panel, wherein the fasteners are configured to engage with each other so as to facilitate donning the vest and securing the vest to one's body. The vest may comprise a material that includes elastin, and the shoulder straps may comprise an elastic material. Some embodiments include an adjustment mechanism for each shoulder strap to enable shoulder strap length adjustment.

With the support member being rigid, or at least semi-rigid, the device may be configured so that when donned by the user and the waist straps are pulled, the support member applies pressure to the user's sacrum while the tension applied to the shoulder strap is adjusted. In such a configuration, the device provides a posture support and retention system during episodes of postural instability to enable individuals to maintain posture and balance while performing functions. The shoulder straps extending from the tensioning system enable generation of force vectors in a direction opposite of those that may be generated by traditional shoulder straps. The rigid support member is disposed in the vest to run parallel with the spinal column, and the shoulder straps and waist straps tie into an anchor located on a portion of the vest directly over the support member. The components, all connected together, work in concert to actively and passively adjust tension and apply pressure to straighten shoulders and improve posture and upper back support.

Physiotherapeutic devices, including the embodiments of physiotherapeutic devices disclosed herein, may be outfitted with sensors to detect statuses and symptoms relevant to the patient and caregiver and to provide reporting and feedback to both the patient and caregiver.

In embodiments, physiotherapeutic devices disclosed herein may include a garment portion having sensors secured thereto, wherein the garment provides posture support to the torso of a user and the sensors generating data indicative of at least one of breathing rate of an individual wearing the brace, movement of the individual, the posture of the individual, change in a position of the individual, the orientation to the ground plane, a heart-related parameter of the individual, a body temperature of the individual, and a sound related parameter associated with the individual, and a processor in electronic communication with the sensors programmed to determine whether the individual has experienced freezing of gate or dyskinesia. Sensors may be selected from the group consisting of a plethysmography band, an accelerometer, a gyroscope, a heart rate monitor, a body temperature monitor, and a microphone. Status may be selected from the group consisting of mood, posture, stability, bradykinesia, compliance with the brace, and falling. An output device may be in communication with the processor, and the processor may be further programmed to cause the output device to provide based on the status of the individual and/or to adjust a parameter of the device based on the detected status of the individual, wherein the parameter is at least one of tightening or loosening a garment support.

In embodiments, physiotherapeutic devices disclosed herein may include detecting a physical state of an individual by storing a plurality of data pairings in a database, wherein each pairing represents an association between at least one sensor datum and a physical state, receiving a transmitted sensor datum, wherein the transmitted sensor datum derives from a sensor that is associated with a garment, and is received at a facility remote to the garment, searching the plurality of data pairings in the database for a physical state associated with the transmitted sensor datum, sending an alert indicating the physical state associated with the transmitted sensor datum, and making a posture support adjustment to the garment based at least in part on receipt of the alert. Sensors may include, but are not limited to, an accelerometer, gyroscope, or magnetometer. Physical state may include, but is not limited to, a state of inactivity, a fall, or a slouch of an individual's torso. In embodiments, an alert may be transmitted to a processor associated with the garment and an action taken at the garment based at least in part on the transmitted alert. An action may include an activation of a motor within the garment, wherein the motor within the garment adjusts tensioners within the garment to adjust the posture of an individual wearing the garment.

In embodiments, physiotherapeutic devices disclosed herein may include detecting a physical state of an individual by storing a plurality of physiological threshold criteria in a database, wherein each criterion among the plurality represents a physiological threshold indicating an individual's physical state requiring medical attention, monitoring sensor data derived from sensors associated with a garment, receiving a transmitted physiological datum from the garment, wherein the transmitted physiological datum is received at a facility remote to the garment, searching the plurality of physiological threshold criteria in the database for at least one physiological threshold indicating the individual's physical state requiring medical attention, and sending a communication to a third party, wherein the communication includes at least an indication of the physical state requiring medical attention and data relating to the individual wearing the garment. A criterion may include a rate of respiration. In embodiments, a communication may be sent to a caregiver, such as a family member, physician, and/or emergency medical services personnel, that is associated with the individual wearing the garment.

In embodiments, physiotherapeutic devices disclosed herein may include a garment portion having sensors secured thereto, wherein the garment provides posture support to the torso of a user and the sensors generating data indicative of at least one of breathing rate of an individual wearing the brace, movement of the individual, the posture of the individual, change in a position of the individual, the orientation to the ground plane, a heart-related parameter of the individual, a body temperature of the individual, and a sound related parameter associated with the individual, and a processor in electronic communication with the sensors programmed to determine the individual's status based on the data from the sensors.

In embodiments, physiotherapeutic devices disclosed herein may include monitoring sensor data derived from sensors affixed to a garment, wherein the garment sensors generate data indicative of a physical state of the garment's user, receiving a transmitted sensor datum from the garment, wherein the transmitted sensor datum is received at a processor remote to the garment, searching a plurality of physical states data stored in a database, detecting at least one physical state associated with the received sensor datum, sending a communication to the user, wherein the communication includes a notice that the at least one physical state was detected and a request for the user to confirm experiencing the detected physical state, and receiving a message from the user confirming that the user is experiencing the detected physical state. In embodiments, the received message may indicate that the user is not experiencing the detected physical state and instead indicate the correct physical state the user is experiencing. In embodiments, the communication may be sent to a mobile phone associated with the user.

While these potential advantages are made possible by technical solutions offered herein, achieving them is not required. The presently disclosed device can be implemented to achieve technical advantages, whether or not these potential advantages, individually or in combinations, are sought or achieved.

These and other systems, methods, objects, features, and advantages of the present disclosure will be apparent to those skilled in the art from the following detailed description of the preferred embodiment and the drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

BRIEF DESCRIPTION OF THE FIGURES

The disclosure and the following detailed description of certain embodiments thereof may be understood by reference to the following figures:

FIG. 3 illustrates a vest configuration with a fabric band where the user's underarm area is free of material;

DETAILED DESCRIPTION OF THE INVENTION

The following description is of an embodiment presently contemplated for carrying out the present invention. This description is not to be taken in a limiting sense, but is made merely for the purpose of describing the general principles and features of the present invention. The scope of the present invention should be determined with reference to the claims.

Figure 1:
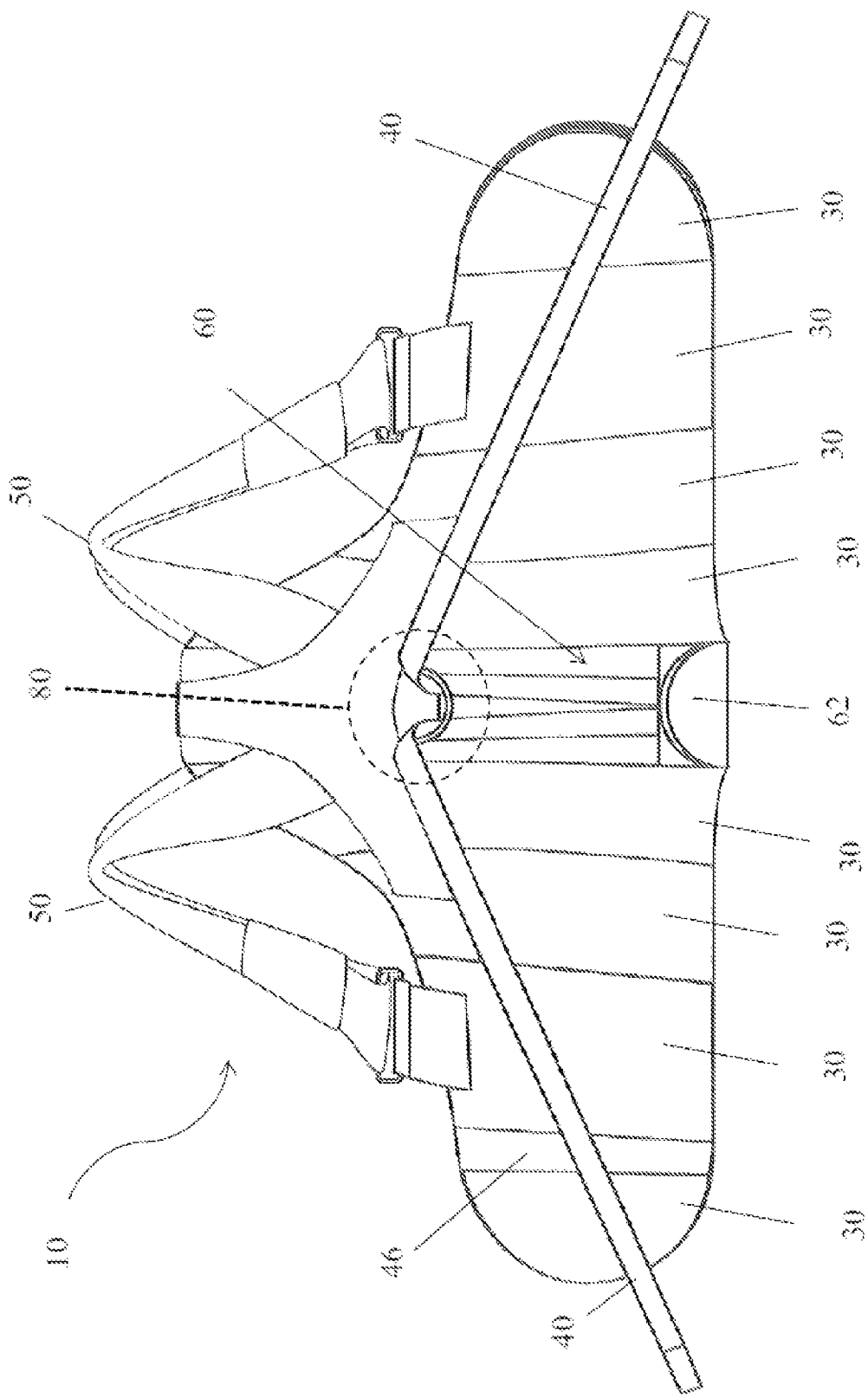
FIG. 1 illustrates an external view of the device, in accordance with an embodiment disclosed herein.
Figure 2:
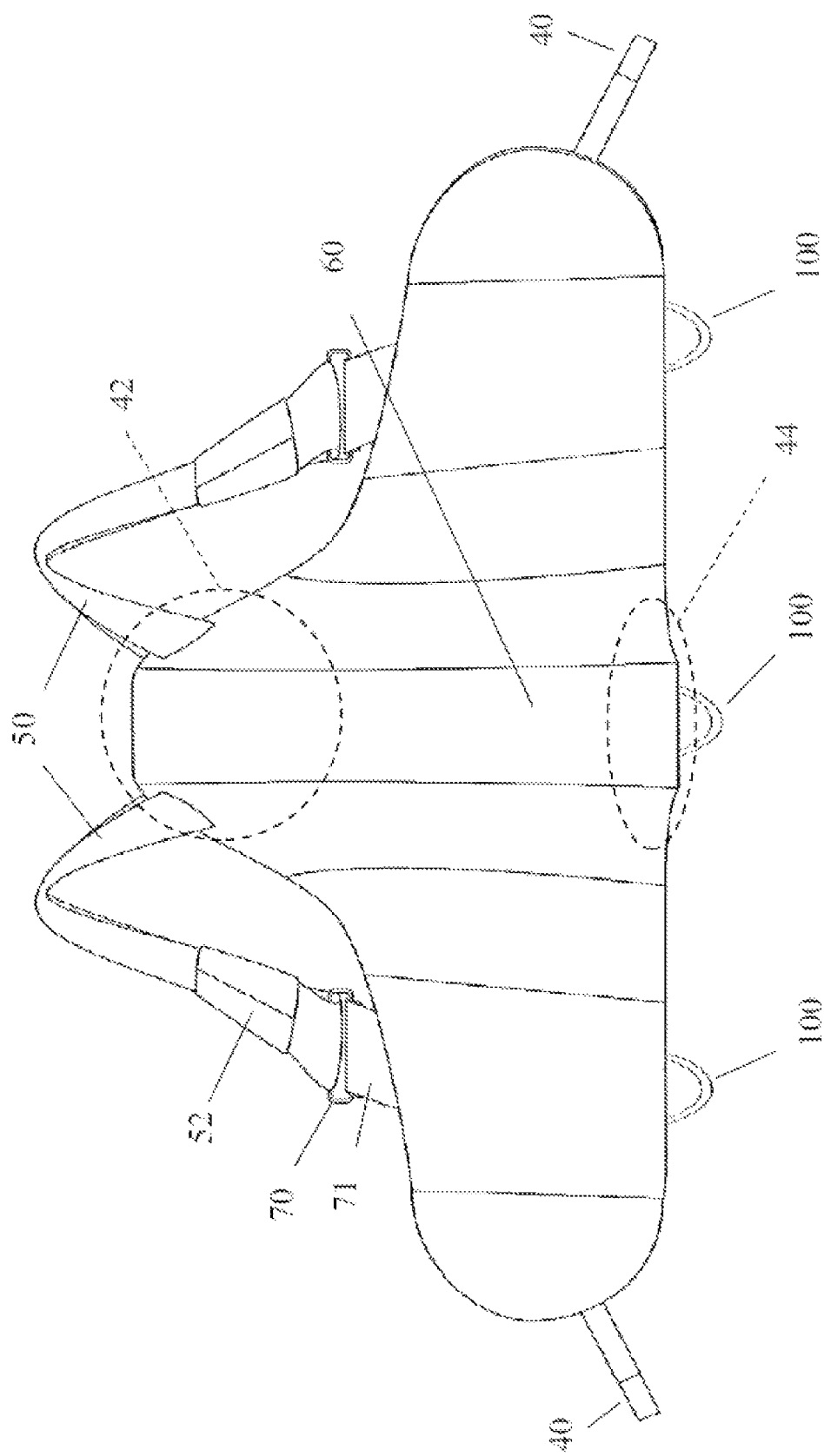
FIG. 2 illustrates an internal view of the device, in accordance with an embodiment disclosed herein.

Referring now to FIGS. 1 and 2, external and internal views of the device 10 are disclosed.

Figure 14:
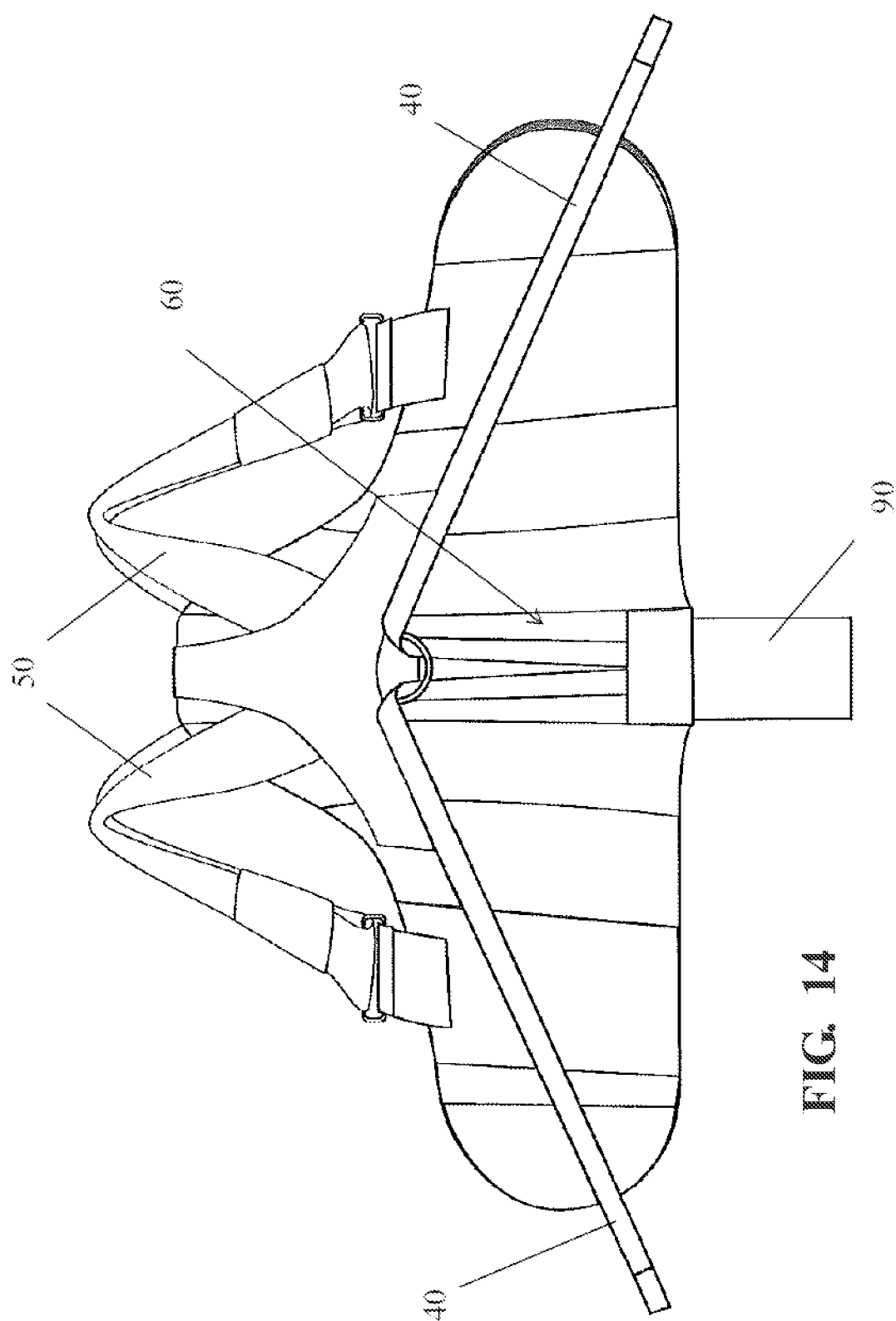
FIG. 14 illustrates another external view with the support member exposed, in accordance with an embodiment disclosed herein.

The device 10 may include a vest 20 segmented into a plurality of segment panels 30 with waist straps 40, shoulder straps 50, a support member 90 (see for example FIG. 14), and a tensioner mechanism 80. A waist tensioning system of the vest 20 may include the waist straps 40, shoulder straps 50, and tensioner mechanism 80. A spine support system of the vest 20 may include the support member 90 and plurality of segment panels 30. As disclosed herein, the waist tensioning system and the spine support system may operate in concert to enable correction and/or maintaining postural stance for individuals suffering from poor posture and/or neurodegenerative disease.

The vest 20, waist straps 40, and shoulder straps 50 may be fabricated from tough, lightweight, textile material such as nylon, cotton, canvas, elastane (i.e., Spandex® brand elastane), etc. Extending around a person's torso, or any portion thereof, when worn, the vest 20 may include an elongated fabric structure with a back portion and two front panels. The back portion has an approximate polygonal shape conjoined with a front panel at each side. The back portion may be configured to rest against a person's back while the front panels may rest against a person's chest and stomach. In such a configuration the vest 20 wraps around a person, substantially enveloping his/her torso. (See FIGS. 17 and 18).

FIG. 1 illustrates the vest 20 in a spread-open, flat position. It can be seen that the vest 20 may widen towards a back portion while becoming narrower towards the two front panels. As seen best in FIG. 2, the middle of the back portion may extend up towards a person's neck, forming a cervical extension portion 42, more so than extending down towards a person's buttock, forming a lumbar extension portion 44. This may be done to provide maximum support and comfort to a user. Generally, a person's posterior torso would require more support, whereas a person's anterior torso would require more mobility and dexterity. Thus, the back portion may be positioned at the posterior torso, whereas the front panels may be configured to connect to each other at a person's anterior torso. This connection may be achieved via fasteners 46, such as hook and pull type fasteners, disposed on surfaces of each front panel configured to engage each other to facilitate a proper and conforming fit of the vest 20 when donned by a user. This configuration may ensure that the vest 20 is comfortably secured onto the wearer, while permitting breathability and enabling the wearer to have a normal range-of-motion. Other types of fasteners for the front panels may include, but are not limited to, snaps, buckles, zippers, etc. It is understood that other configurations may be utilized as well, such as a narrowing towards the back portion, widening at a front panel, or even having the narrowest portion at a user's midsection or waistline.

The back portion, front panels, cervical expansion portion, and lumbar expansion portion may be generated form a unitary piece of fabric. Alternatively, each portion may be a separate section that is sewn together or even reversibly attached to each other via a zipper, hook-and-pull type fastener, etc.

The segment panels 30 may be integral to the vest 20 or may be removable and interchangeable sections of the vest 20. Each segment panel 30 may be defined by a change in elasticity, stiffness, and/or rigidity. While the drawings depict a different elasticity for each adjacent segment panel 30, one skilled in the art, with the benefit of the present disclosure, will appreciate that all segment panels 30 may exhibit the same elasticity, all may exhibit a different elasticity, or any combination thereof. The segment panels 30 are shown to have a length that is longer than the width; however, the width may be longer than the length, or any other combination of width-to-length ratios may be utilized. Furthermore, some segment panels 30 may exhibit elasticity in one direction while another may exhibit elasticity in a different direction. In one embodiment, the elasticity of each segment panel 30 is the width direction.

One embodiment may include some segment panels 30 that are elastic and some that are not. For example, a vest 20 may include four segment panels 30 either side of the support member pouch 60, wherein the two outer most segment panels 30 on either side are not elastic and the two inner most segment panels 30 on either side are elastic. This configuration may be done to provide maximum support and therapeutic effect. The two inner most segment panels 30 lie against the user's torso more directly that those of the two outer most segment panels 30. Consequently, therapeutic effects may be more effectively realized by having the configuration described above. One skilled in the art will appreciate, with the benefit of the present disclosure, that other combinations of elastic and non-elastic segment panels 30 may be utilized.

The widths of the segment panels 30 may be based on how much stretch is desired for compression of the individual's body to provide circumferential pressure for therapeutic effect. This may be calculated using the elastic properties of the braces materials. The widths of the segment panels 30 may also be based upon desired stretch for sizing purposes. The length of the segment panels 30 may be based of the anatomical positioning of the segment panels 30 on the vest 20. Each segment panel 30 rests along the user's body and there height is determined based on where pressure should be applied to the user to obtain therapeutic effect.

This may be done to accommodate persons of various weights, waist size, height, and/or whether the vest is being worn overtop or underneath clothing. A segmented panel 30 configuration may also provide desired levels of support, pressure, and dexterity at certain points of a person's torso. For example, although a person may require less support in the anterior torso, she may still require support so segment panels 30 in the abdominal region may be more rigid. While therapeutic effects of the vest 20 via the segment panels 30 are normally achieved by the panels 30 working in conjunction with the other components of the vest 20, a desired physiotherapeutic effect may be achieved by applying pressure at an oblique section via a segment panel 30.

Other therapeutic effects may be realized from the various configurations of the segment panels 20. For example, different combinations of elastic and non-elastic segment panels 30, as well as varying degrees of elasticity, may be utilized to modify comfort levels, balancing, and posture.

At least one waist strap 40 may be provided with the vest 20, which may be attached to a portion of the support member pouch 60 via a first end of the waist strap 40, whereas the second end of the waste strap 40 is free. The free end may be configured to extend vertically up through the tensioner mechanism 80. The strap 40 may then loop around a user's waist to be connected to the vest 20, or to another free end of a second waist strap 40, to not be connected at all, or not even wrapped around the waist of the user. (See FIGS. 17 and 18). The waist strap 40 may enable application of the tensioning system by a user. For example, pulling the waist strap 50 adjusts tension applied to shoulder straps 50 and the support member 90 so that pressure is applied to the sacrum of the wearer, and stability and support are provided for the shoulders and entire torso. Details of the tensioning and spine support systems of the vest 20, and how they generate proper force vectors to assist with posture and other therapeutic functions will be discussed later.

The first end of the waist strap 40 may be permanently affixed to the vest 20 via stitching. Alternatively, it may be reversibly secured via a central fastener 62. The central fastener 62 may include a hook and pull type securement, and may also be configured to retain the support member 90 within the support member pouch 60 by covering and concealing an opening leading into the support member pouch 60. For example, both ends of the waist strap 40 may be provided with complementary hook and pull type fasteners, and the support member pouch 60 and the central fastener 62 may be provided with additional complementary hook and pull type fasteners. Furthermore, the central fastener 62 may be configured as a flap that is permanently affixed to a bottom portion of the vest 20. An end of the waist strap 40 may be secured to the central fastener 62 and the opposite end may be routed up through the tensioner mechanism 80, as described earlier. Concurrently, the support member 90 may be placed within the support member pouch 60 and secured in place with the central fastener 62, thereby providing proper and adequate securement for both the waist straps 40 and the support member 90.

Figure 17:
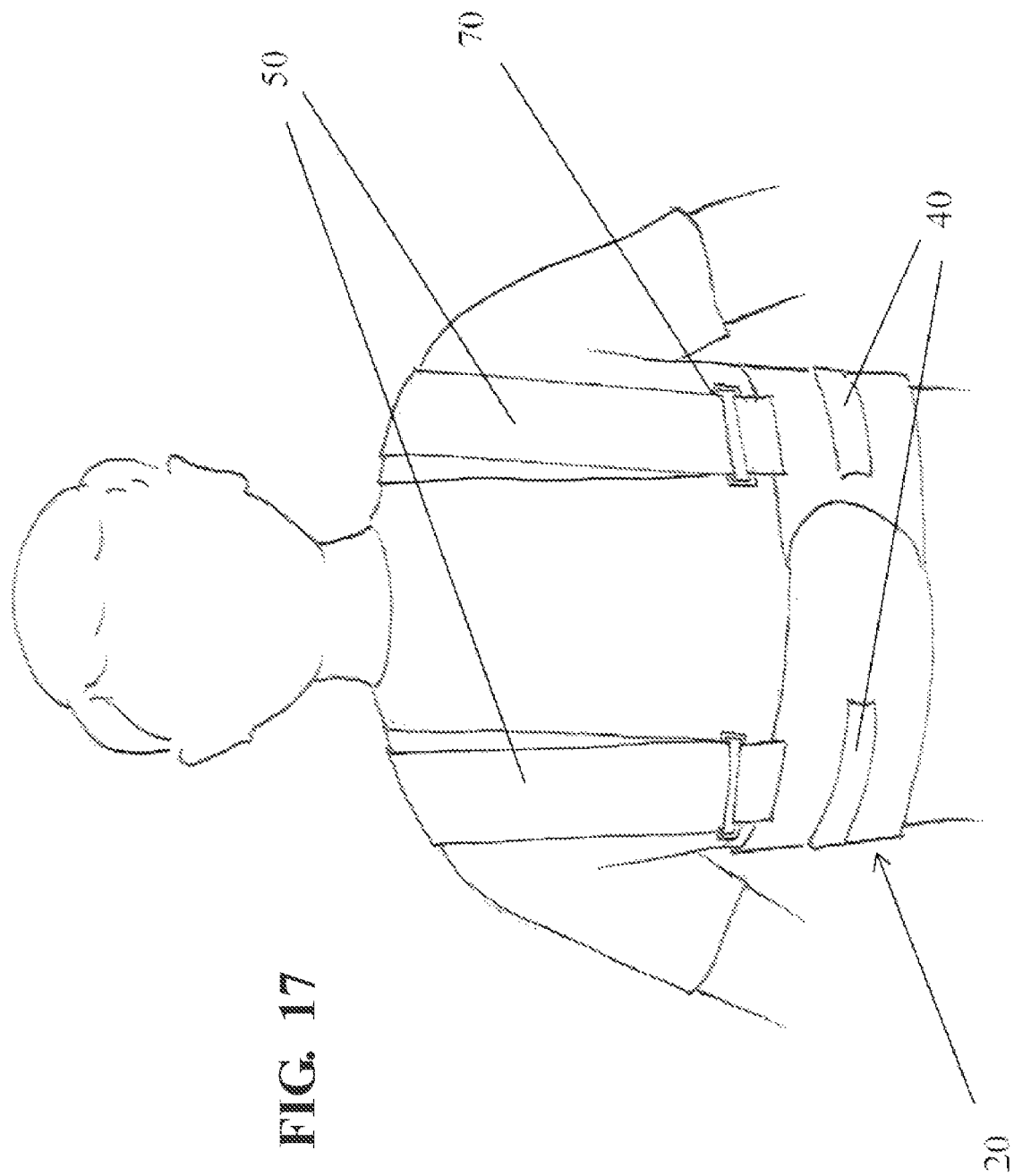
FIG. 17 is an environmental front view of a user donning the device.
Figure 18:
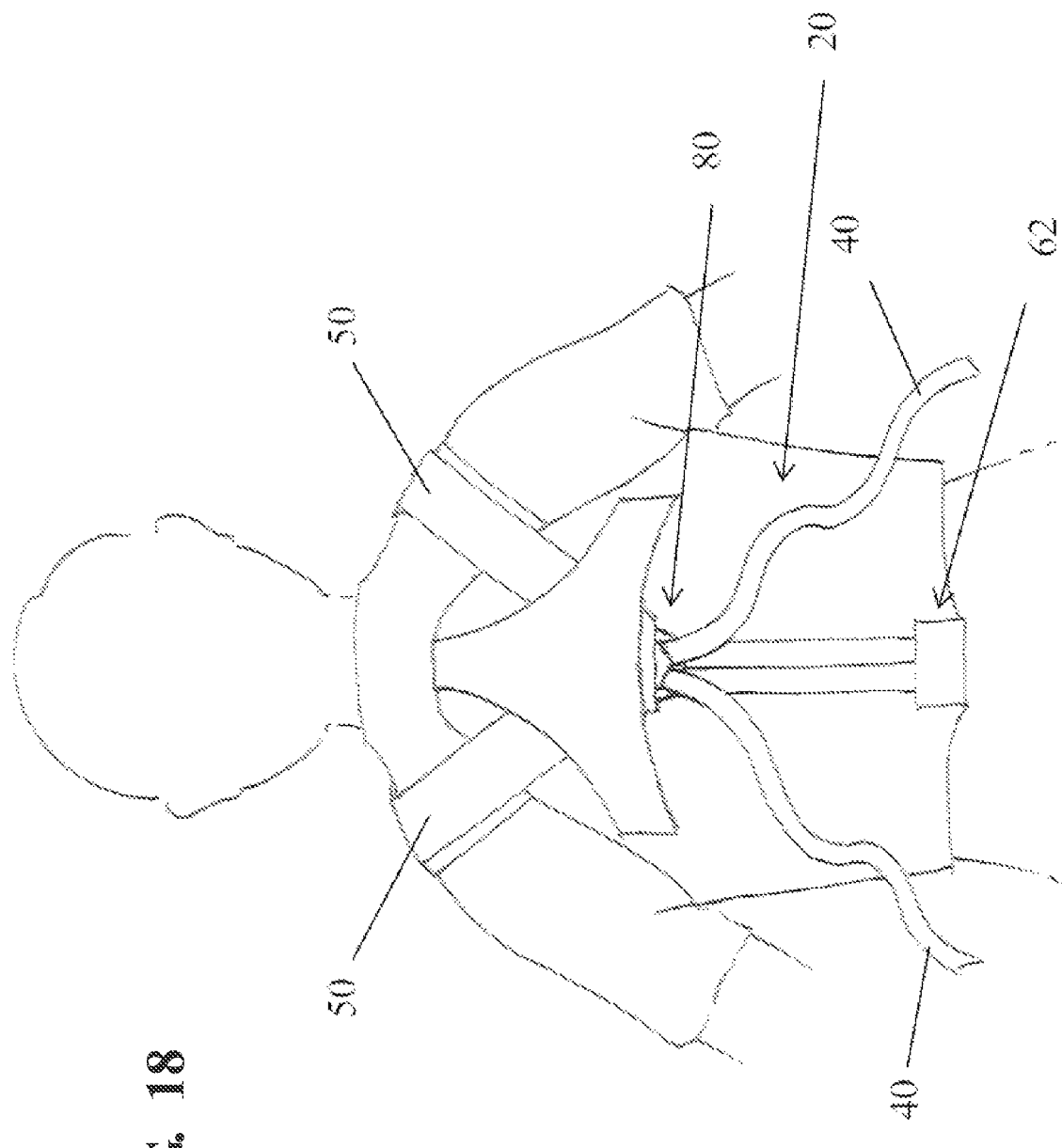
FIG. 18 is an environmental rear view of a user donning the device.

The free ends of the waist straps 40 may also include a fastener to enable a user to wrap and/or "stow" the waist straps 40 when not in use by wrapping the straps 40 around the vest 20 and securing the straps 40 to each other or to another complementary fastener located on the vest 20, as shown in FIG. 17.

Figure 15:
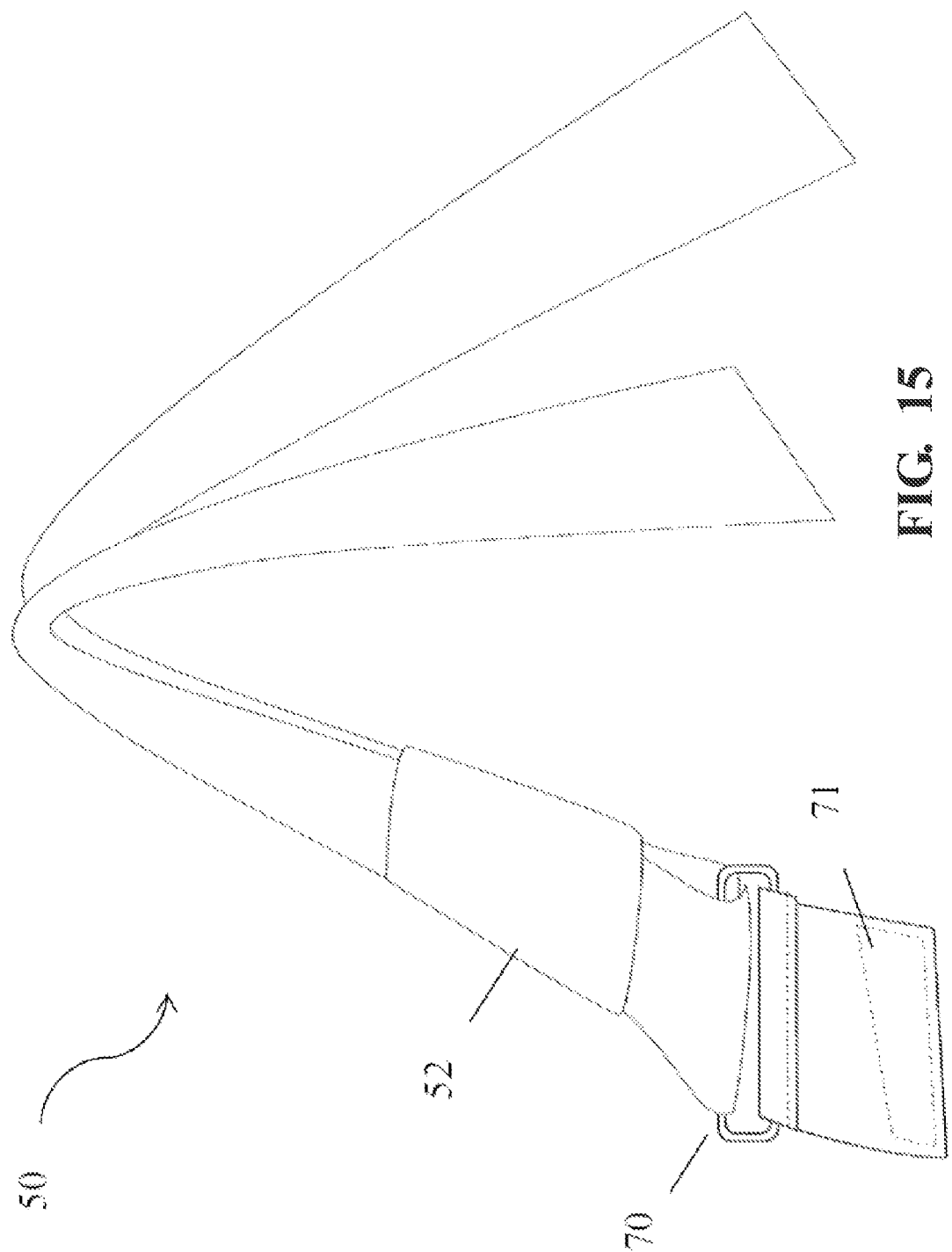
FIG. 15 illustrates a side view of the shoulder straps of the device, with the vest portion omitted for ease of illustration, in accordance with an embodiment disclosed herein.
Figure 16:
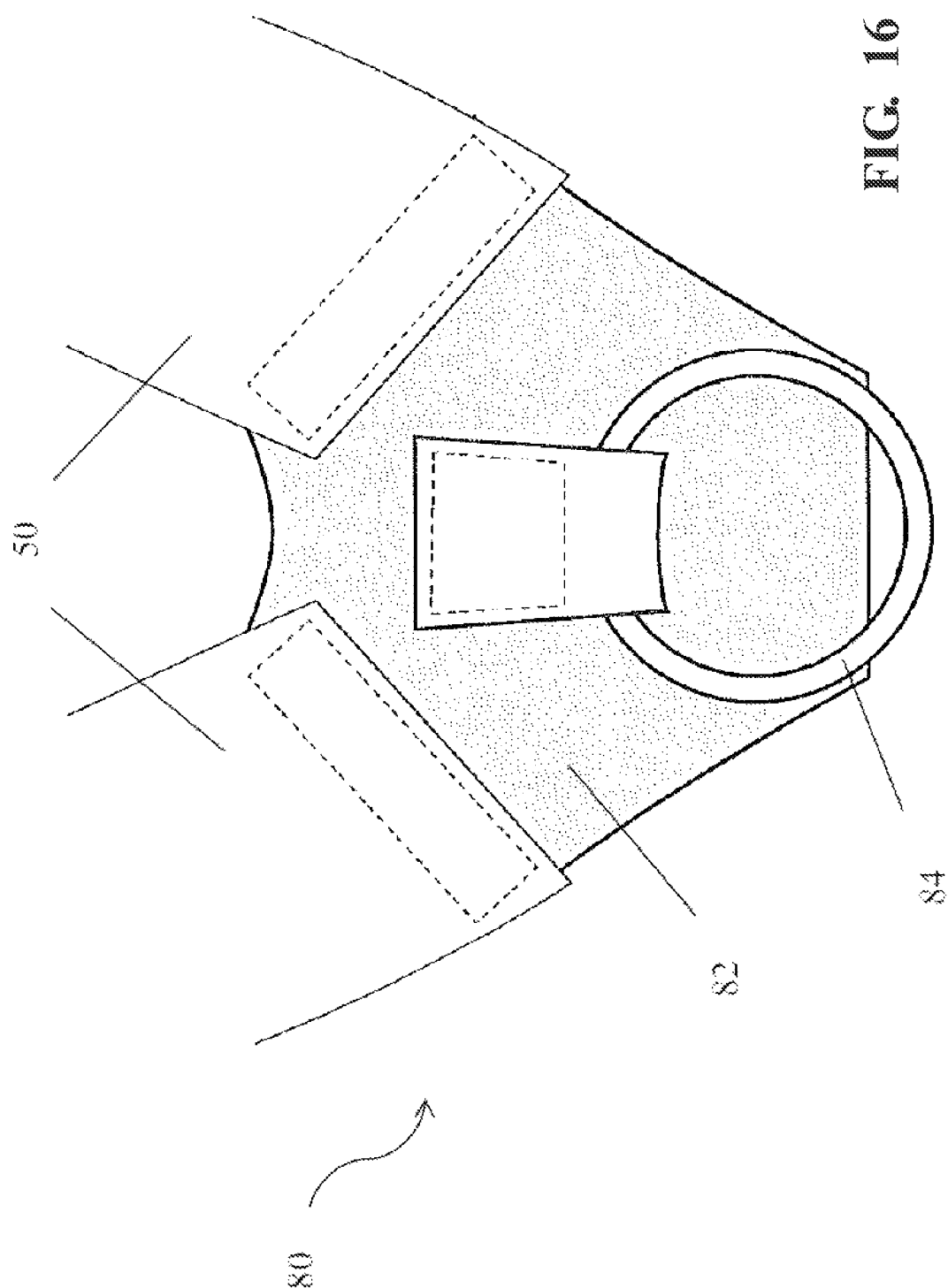
FIG. 16 illustrates an exploded partial view of the tensioner mechanism, in accordance with an embodiment disclosed herein.

The device 10 may include at least one shoulder strap 50 extending from a top, rear portion of the vest 20, and may be attached via stitching at a first end, whereas the second end may be attached to a central member 82 of the tensioner mechanism 80 (See FIG. 15). An adjustment mechanism 70, for example, a buckle, may be provided to adjust the length of each strap 50. A shoulder pad 52 may be included with the shoulder strap 50 to provide added support and comfort for a user, which may include a sleeve with padding disposed on a surface thereof. The shoulder pads 52 may also keep portions of the shoulder straps 50 aligned, thus making it easier to don the device. Any portion of the shoulder strap 50 may be elastic to assist with directing and balancing force vectors and to provide a desired therapeutic effect and/or comfort. For example, the first end may be connected to the vest via elastic extenders 71. (See FIG. 16). Each shoulder strap 50 may be constructed of a single, elastic member so as to exhibit a consistent stretch. Each shoulder strap 50 may exhibit the same elasticity as the other shoulder strap 50, further providing consistent support for a user employing the device 10. Changing the width of each strap 50 may be done to modify the amount of force applied to move the shoulders back into the correct therapeutic position.

The vest 20 may be provided with a support member pouch 60 that is substantially in alignment with a user's spine when the vest 20 is donned. The support member pouch 60 may be configured to receive and retain a support member 90. At last one support member 90 may be inserted into the support member pouch 60 by sliding it through, and it may be held in place by the central fastener 62 in a similar manner described above. Alternatively, the support member 90 may be reversibly inserted via sliding through an opening at a top of the support member pouch 60, wherein the bottom of the support member pouch 62 may be sealed. Alternatively, or in addition, any number of support members 90 may be permanently secured within the support member pouch 60 via other methods, such as stitching. Furthermore, a first support member 90 may be permanently secured within the support member pouch 60 via stitching while other support members 60 may be reversibly secured via the central fastener 62.

In addition, any support member 90 may be integral to the vest 20. For example, the vest may include a central panel 30 that has the stiffness and rigidity to serve as the support member 90. Removing the support member 90 at the discretion of a user may be beneficial to facilitate cleaning and maintenance of the device 10.

The support member 90 is a rigid and/or semi-rigid structure, such as a plate for example, which may be fabricated from aluminum, steel, plastic, composite fiber, etc. After the vest 20 has been donned and secured against a user's body, the support member 90 places pressure against the sacrum to serve as a fulcrum for bearing the load being applied at the shoulder straps 50 as a user performs functions such as walking, sitting, standing, moving, etc. The support member 90 may have dimensions of 3¼-6¼ inches wide and 16-24 inches high. The width may be based upon the location of the paraspinal muscles. The support member 90 preferably span the width of the gap between these muscles to create the therapeutic effect desired without painful pressure on the spine. The height may be based on the height of the individual specified for each size of the brace. While the support member 90, combined with the straps 50 and main band of the vest 20, provide therapeutic effect, the full correction of posture may best be achieved once the individual has tensioned the straps 50 using the waist straps 40 to force the shoulders back and into the correct position.

A tensioner mechanism 80 may be disposed on a rear portion of the vest 20, which may be provided with a central member 82 in mechanical connection with an anchor 84, such as a D-ring, an O-ring, a buckle, a pulley, shackle, etc. that may facilitate routing at least one waist strap 40 and enable sliding of the waist strap 40 so as to adjust tensioning of the tensioning system. Pulling on the waist strap 40 acts upon the central member 82, whereby it transfers force in a controlled manner to lift the shoulders via the shoulder straps 50 and ensures that the support member 90 is in proper position to act upon the sacrum.

As described earlier, the segment panel 30, waist straps 40, shoulder straps 50, tensioner mechanism 80, and support member 90 all act in concert to generate a postural correcting system that enables complete support of the spine, shoulders, and waist. For example, a second end of each shoulder strap 50 meets the tensioner mechanism 80 posteriorly along a cervical extension portion 42 to provide complete, balanced upper back support to the wearer. This configuration ensures that pulling on the waist straps 40 results in pulling the shoulder's back, which in conjunction with the other features of the device 10, provides the complete, balanced upper back support. This intersection is attached to the waist tensioning system via the anchor 84 that may move vertically, due to the central member 82, across a thoracic region of the vest 20 when subjected to variations in force vectors. A user may use the waist straps 40 to easily apply force in an ergonomic horizontal direction, which is transmitted into a vertical force via the tensioner mechanism 80 to act upon the shoulder straps 50 and support member 90, thereby providing the wearer with the proper postural-correcting forces for their upper back and shoulders. Thus, pulling on the waist straps 40 enables a user to supply the desired level of posture support, while the other features of the vest 20 continue to provide therapeutic effects.

The segment panels 30 provide additional support and therapeutic pressure at certain portions of the body. The pressure provided by the device 10 is a circumferential pressure around the trunk of the user. This may relieve pressure in the lower back and may help push the user against the support member 90.

Once comfortably secured to a user's body, a single active motion (e.g., pulling the waist straps) of the waist straps 40 may provide support and therapeutic effects from multiple components of the device 10. Components, such as the support member 90 and segment panel 30, provide passive posture and therapeutic support without actuation of the waist straps 40. These components may provide passive support in addition to providing active support. The ease of use and effectiveness of the device 10 renders the vest 20 well suited for users suffering from neurodegenerative type disease.

In an alternative embodiment, a system of cross-straps positioned at both the front of the vest 20 and the back of the vest 20 may be provided. Actuating the waist straps 40 would automatically provide the shoulders of the wearer with enough tension to maintain an upright position. This would enable proper support and posturing with an actuation of a single waist strap 40, whereas actuation of both waist straps may be required to generate the same effect without the cross-strap configuration. This adds convenience for a user because activation of the tensioning system to affect the entire back may be achieved by actuation of a single waist strap 40.

In an alternative embodiment, a shoelace corset system installed within the vest 20 may be used to increase the support provided by the device 10. The shoelace corset system operates via a drawstring and cord lock mechanism. The cord lock mechanism is configured to reversibly secure the drawstring at a desired position when drawn through the lock mechanism. The drawstring may be connected to a lace-network that when acted upon circumferentially withdrawals the vest 20, or at least portions thereof, to generate a conforming fit to a user's body.

In an alternative embodiment, the vest 20 includes at least one belt loop 100 located at a bottom rear portion of the vest 20 and that is configured to reversibly attach to trousers of a user. (See FIG. 2). Tensioning system straps may be provided at the front of the vest 20 and configured to be pulled downward by the user. Upon pulling the tensioning straps, the central member 82 is acted upon, as described above, to generate the force vectors necessary to correct and/or maintain posture while the spine system provides postural support.

In an alternative embodiment, a multi-gear system that may include a winch, may be included with the vest to assist with providing and/or maintaining proper tensioning and postural support. The winch may be located within the vest 20. The winch may be used to set a desired level of tension and support by selectively drawing/releasing/locking tensioning cables. A cable network extends from the winch and may be attached to various portions of the vest 20, including the tensioning mechanism 80. The winch may be mechanical or electro-mechanical. The winch may be easily accessible from the front of the vest 20, and it may be operable by hand or remote control. Some embodiments may include a simple two-gear system.

In an alternative embodiment, portions of the vest 20 may include inflatable sections and/or bladders that may be inflatable via fluid, such as water, air, etc. The inflatable sections may be configured to reversibly and/or permanently retain bladders. In either case, the bladder includes a valve suitable for selectively inflating and deflating the bladder at the discretion of the user. In a situation where the bladder is permanently retained within the inflatable section, a valve stem may be provided that extends through the vest 20. By inflating certain sections and to certain pressures, tension and support can be more easily tailored to accommodate the condition that a user is immediately encountering.

Figure 4A:
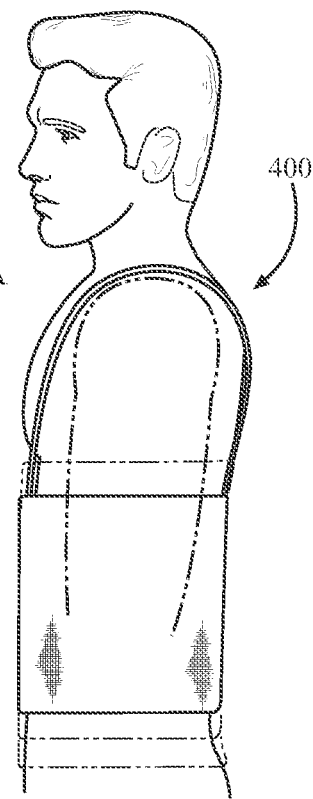
FIG. 4A illustrates a vest configuration where the shoulder straps attach to the back portion of the fabric band.
Figure 4B:
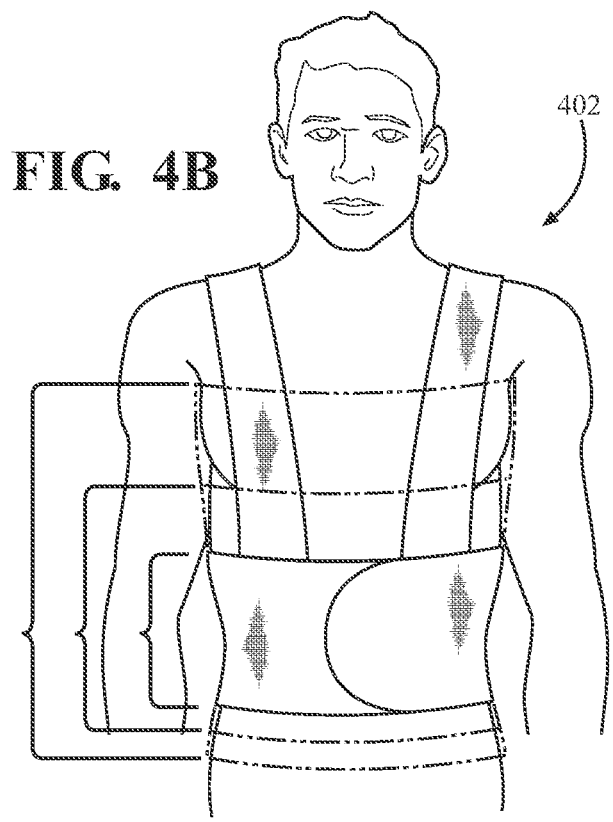
FIG. 4B illustrates a vest configuration in which a plurality of band widths may be utilized.
Figure 5:
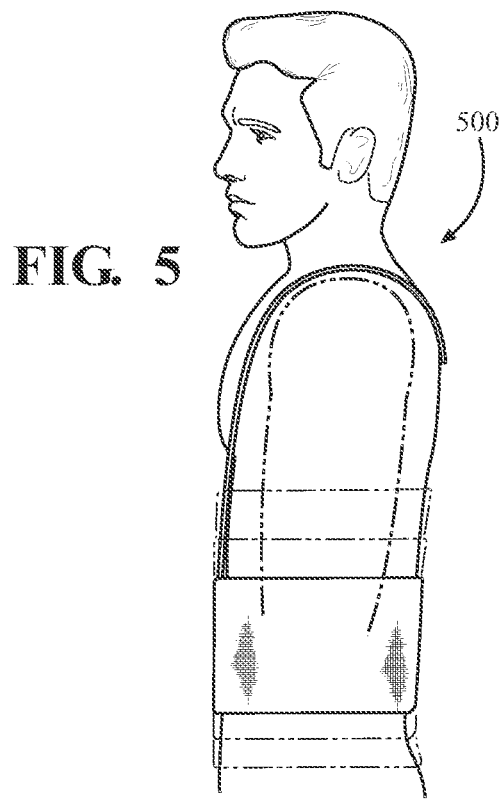
FIG. 5 illustrates a vest configuration in which a band along the lower body portion includes straps that connect to the upper portion of the band and continue over the shoulders that does not connect to the back of the vest.
Figure 7:
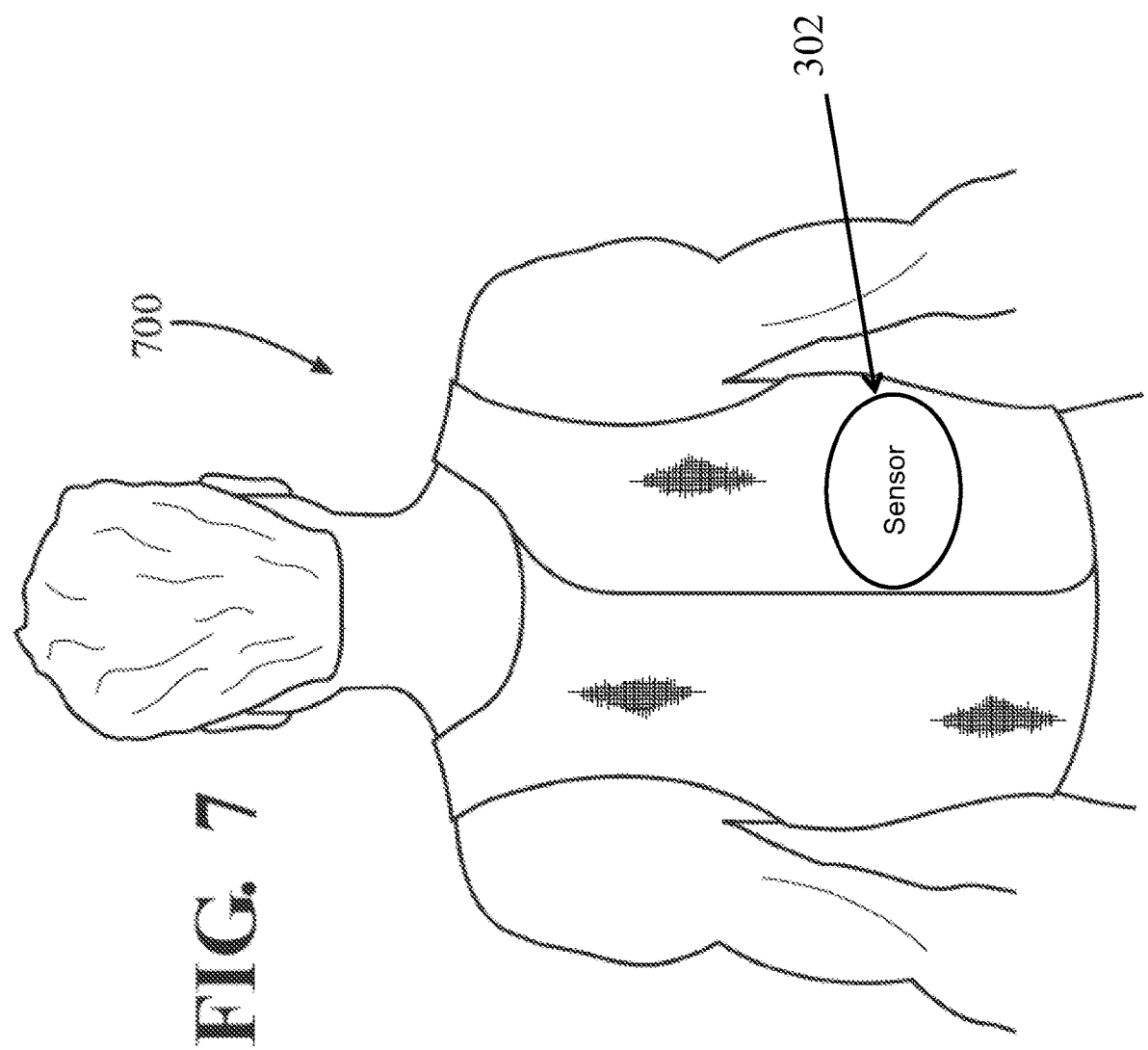
FIG. 7 illustrates a vest configuration with a front apron having a high profile that continues upwards to the collar bone.
Figure 6:
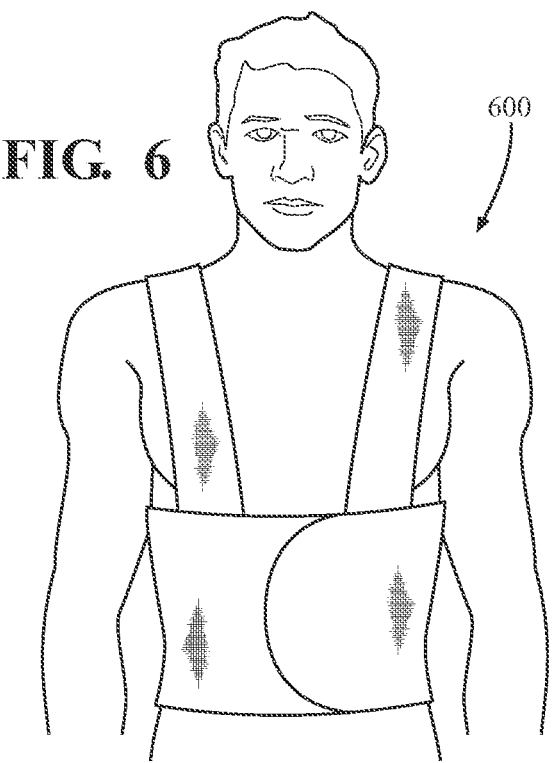
FIG. 6 illustrates a vest configuration with a front apron with a lowered profile that sits below the breast plate.
Figure 8:
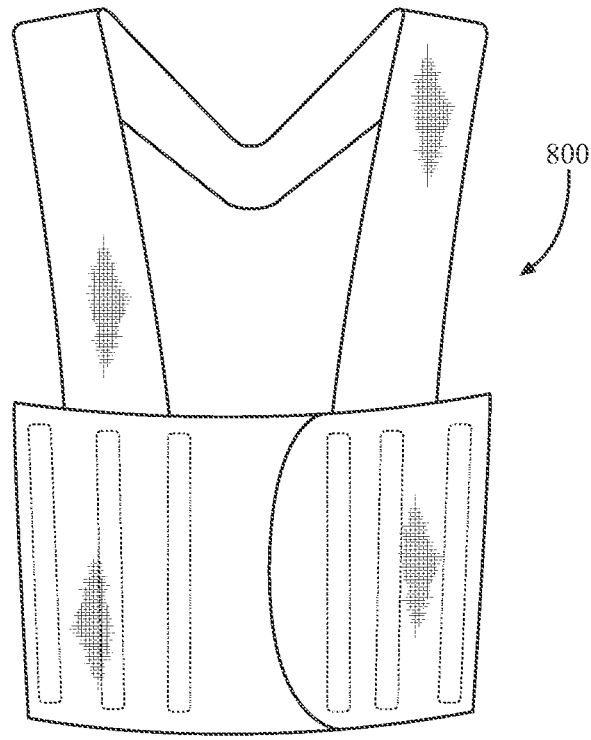
FIG. 8 illustrates depicts semi-rigid support members built into the front and side of the vest.
Figure 9:
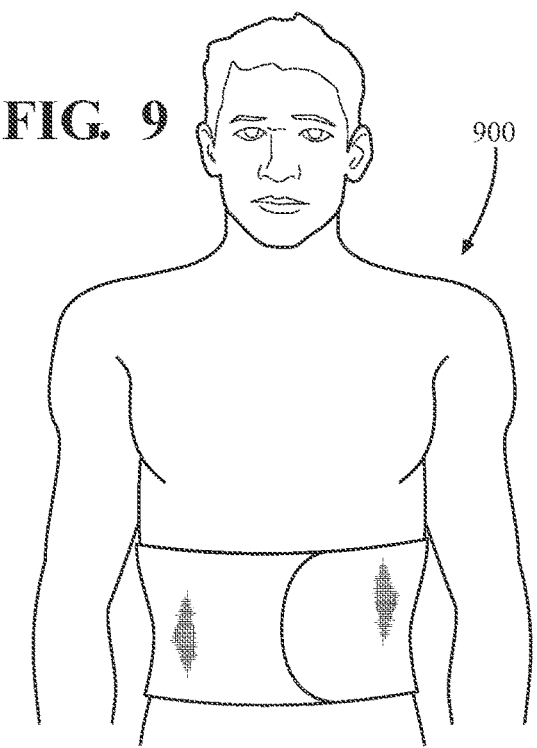
FIG. 9 illustrates a vest configuration having a single strap closure that allows for continued fastening.
Figure 10:
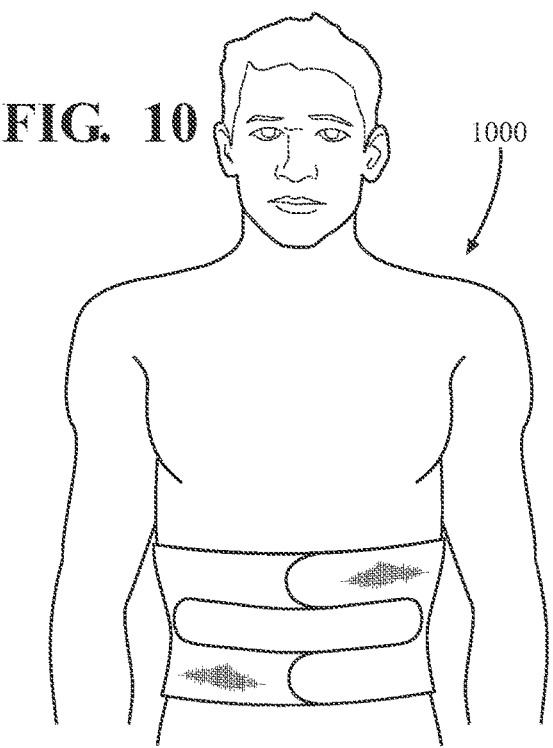
FIG. 10 illustrates a vest configuration having a multi-strap closure that allows for continued fastening.

In an example embodiment, and referring to FIG. 3, the vest configuration 300 may include a fabric band where the user's underarm area is free of material in order to provide room for comfort, such as during movement. The lowered profile may also prevent the brace aggravating the underarm area of a user. Referring to FIGS. 4A and 4B, the fabric band of the vest may be of any thickness along the lower body 402 with one or more straps that connect to the upper portion of the band 400 and continue over the shoulders that connects to the back of the vest. Although the band is referred to here as a fabric band it should be understood by one skilled in the art that the band may be made of other materials, including but not limited to synthetic material, plastic, rubber, synthetic rubber, elastic, foam, or some other type of material. Referring to FIG. 5, the vest may include a band along the lower body portion with straps that connect to the upper portion of the band and continue over the shoulders that does not connect to the back of the vest 500. As shown in FIG. 6, the vest's front apron may have a lowered profile that sits below the breast plate 600, and the vest's front apron may have a high profile that continues upwards to the collar bone 700, as shown in FIG. 7. FIG. 8 depicts semi-rigid support members built into the front and side of the vest 800. In an embodiment, the vest may be closed using any closure method that allows for continued fastening, as described herein. The vest may provide circumferential pressure to the trunk of a user with a wide band that is fixed around the trunk of the user, and that provides compression. As shown in FIG. 9, the vest may have a single strap closure that allows for continued fastening 900, or a multi-strap closure that allows for continued fastening 1000, as shown in FIG. 10.

Figure 11:
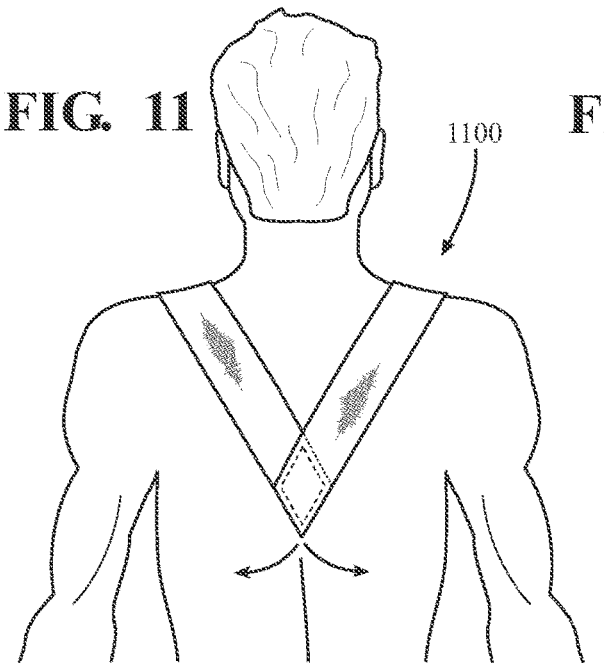
FIG. 11 illustrates a vest configuration in which the shoulder straps of the brace are vertically positioned so that the straps attach to the band and route over a user's shoulders to attach together in the back to form a "V" shape.
Figure 12:
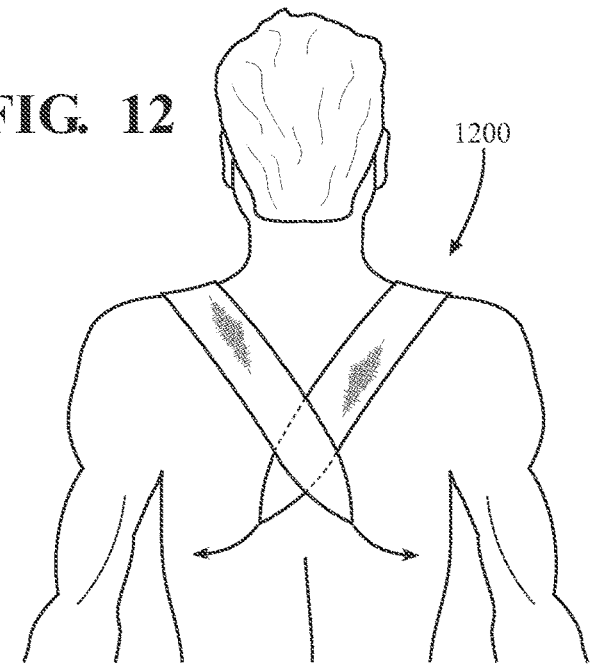
FIG. 12 illustrates a vest configuration in which the straps attach in the front of the brace, extend over a user's shoulders, cross in the back, and attach independently to tensioning devices of the brace.

In an example embodiment, the shoulder straps of the brace, as described herein, may be vertically positioned so that the straps attach to the band and route over a user's shoulders to attach together in the back to form a "V" shape 1100, as shown in FIG. 11. The straps may be single or double layered, may form a pulley system, may be routed to the front of the brace through a loop and back over the shoulders towards the back, and may have padding. The straps may be positioned at an angle in the front of the vest so that the straps can continue in the back of the vest to form a "V" shape, and may be positioned at any angle in the front of the vest to form a "V." The straps may be made of elastic or some material capable of stretching along an axis parallel to the band and/or along an axis perpendicular to the band. The straps may attach in the front of the brace, extend over a user's shoulders, cross in the back, and attach independently to tensioning devices of the brace, as shown in 1200. The straps may attach in the front of the brace and cross before reaching the user's shoulders in an "X" pattern, to continue down the user's back. The straps may attach in the front and cross before reaching the user's shoulders to cross in the back and attach the back of the brace.

In embodiments, a tensioner in the form of "X" shaped anterior straps may adjust the torso twisting of a user. This waist tensioner may provide circumferential pressure to trunk of a user, and a wide band that is fixed around the trunk of the user may provide compression. The waist tensioner may be in a single-belt or a multi-belt form to provide circumferential pressure to the trunk of a user. Tensioning may be elastic-based in order to increase tensioning pressure. In another embodiment, tensioning may be provided by manual tensioning cables or straps that extend over a user's shoulders. Such tensioning cables or straps may fasten around the user's trunk and a winch system may be provided to pull tensioning straps. A user may dial a winch to manually adjust the degree of shoulder strap and waist tension. It should be understood that the winch may be placed on a plurality of locations of the brace, depending in part on the other features provided in the brace, as described herein. A winch may be electrically operated. In an example, a user may push a button to engage, activate, control, and/or deactivate the shoulder and waist tensioning systems winch. In another embodiment, a user may input the level of tension wanted, and the winch may then automatically adjust to the user-specified tension level. A tensioning gage may be provided for measuring and assessing the tension levels of the brace.

In embodiments, the front panel of the brace may consist of a single unit. This single unit may be made of one continuous piece of fabric, or segmented into multiple pieces of fabric.

In embodiments, the back panel of the brace may consist of a single unit. This single unit may be made of one continuous piece of fabric, or segmented into multiple pieces of fabric.

In embodiments, a tension anchor may be provided by the brace at a point where the straps attach to the tensioning mechanism. A ring configuration may be provided in the form of a connected metal, plastic, or fabric object shaped in any form, and through which the tensioning mechanism can be threaded. A buckle may be provided as a rigid attachment point from the tensioning mechanism to the straps. A pulley may be provided in the form of a metal, plastic, or fabric pulley shaped in any form through which the tensioning mechanism can be threaded. A shackle may provide a rigid attachment point from the tensioning mechanism to the straps. A hinge may provide a rigid attachment point from the tensioning mechanism to the straps. A fixed, rigid point attachment may be provided at a point between the tensioning mechanism and the straps.

In embodiments, posterior support (e.g., spine support) may be provided by the brace. A sacrum support member may reside in a support member pouch on the posterior, in the lower torso region of the brace. This sacrum support member pouch may be open at the top, may be permanently sealed (e.g., stitched shut), or have some other configuration. A cervical extension member may be provided in the form of a rigid panel. This panel may be provided in an open or closed pouch of the brace. A lumbar extension member may be provided in the form of a rigid brace. This panel may be provided in an open or closed pouch of the brace. A support member, posterior, sacrum, cervical and/or lumbar may have variable width, length and/or thicknesses.

In embodiments, the brace may include padding (e.g., to provide greater comfort for a user). Such padding may be provided in the shoulder region, back region, anterior torso region, underarm region, front region, or some other area of the brace.

In embodiments, the brace may include a device for adjusting pressure/tension that is connected along various point(s) along the spine. The device will fill up to provide pressure and tension.

In embodiments, the brace may include an adjustable bladder. The bladder may be of a fixed pressure (e.g., to achieve recommended posture angle). The bladder may be an air bladder. The air bladder may be further associated with a manual pump mechanism and/or motorized pump mechanism that allows the user to adjust the air pressure. In another embodiment, the bladder may be a fluid bladder. The fluid bladder may be filled with water, gel or some other liquid material. In another embodiment, posture adjustment may be provided by a foam pad within or on the brace. In another embodiment, posture adjustment may be provided by a rigid plastic or metal device that may be placed on a rigid back panel of the brace to achieve recommended posture angle.

In embodiments, methods and systems for securing the position of the brace may include a belt loop, such as one secured around a user's trunk. This loop may be made of a stretchable or rigid material.

In embodiments, methods and systems for securing the position of the brace may include a rappelling-type leg strap, where such straps are configured around a user's legs and attach to the brace.

Figure 13:
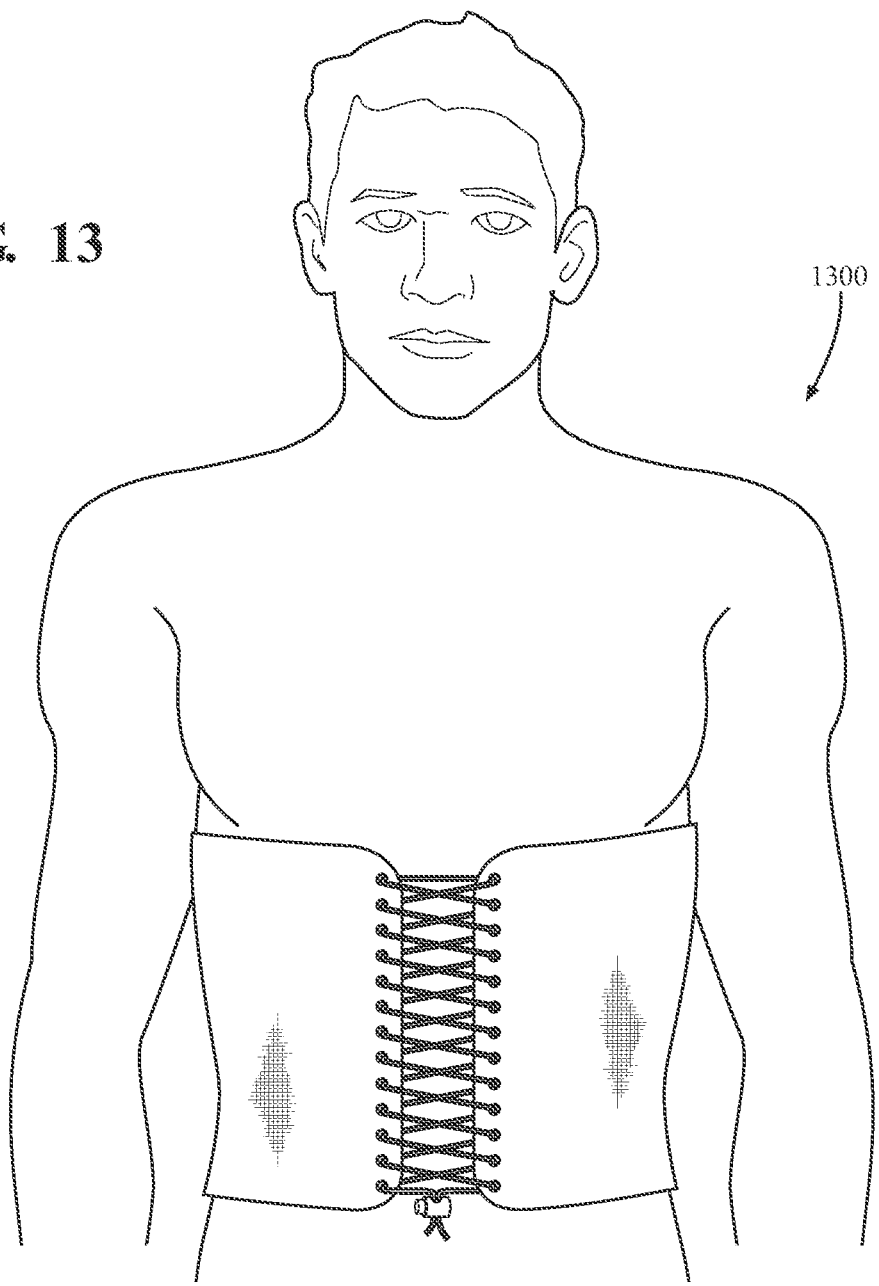
FIG. 13 illustrates vest configuration in a bodice form with a cord-lock type mechanism.

In embodiments, the form factor of the brace may include, but is not limited to, a vest, a shirt, a blouse (or a integrated into a shirt or blouse), a corset or bodice (e.g., with a cord-lock type mechanism 1300, as shown in FIG. 13, a jumpsuit (or integrated within a jumpsuit), a uniform or some other garment type.

In embodiments, the materials of the brace may include, but are not limited to, nylon, cotton, canvas, elastane (e.g., Spandex), fabric, plastic, metal, or some other type of material.

In embodiments, the materials used for support members may include, but are not limited to, aluminum, steel, plastic (including thermaform plastic, such as molded to a user's back shape and/or target posture position), composite fiber, plastic, metal, or some other type of material.

In embodiments, the fastener types used in the brace may include, but are not limited to, Velcro, snaps, buckles, zippers, buttons, magnets, hook-and-pull, laces, or some other type of fastener, including fastener types that allow for a rigid connection.

In embodiments, the brace will contain or be in communication with at least one sensor 302, which will hereinafter be referred to as sensors as shown schematically in FIG. 3. Sensors 302, and the locations of such sensors 302, vary based on the particular parameter being detected. Sensor types used in the brace and/or associated with the brace may include, but are not limited to, off-the-shelf sensors, thermometer, accelerometer, magnetometer, gyroscope, humidity gauge, barometer, respirometer, heart rate monitor, EMG, EKG, EEG, microphone, GPS, air monitor, light monitor, body temperature gauge, pressure monitor, tension monitor, strain gauge, galvanic skin response monitor, glucose monitor, hydration monitor, or some other type of gauge, monitor or sensor, including wearable devices, including fitness monitors used to measure, record and store steps taken by a user or some other activity and/or health status of the user. While FIGS. 3 and 7 schematically shows sensors 302, it does not show the locations of the sensor 302 on the brace or the type of sensors 302 used for particular monitoring situations. The table below presents sample embodiments of sensor type, symptom of a user for which the sensor may be used to monitor, measure, record and share data, location of the sensors, and a sample embodiment of how such monitoring may be achieved by the methods and systems of the disclosure, as described herein:

| Sensor | Symptom | How to Monitor |
| --- | --- | --- |
| Plesmography (breathing rate) | Fall potential, Postural Instability, freezing of gate, tremor, dyskinesia, falling, On Off medication | Use algorithm to determine if readings are indicative of symptoms combined with other sensors Placed around users chest in the brace. |
| Accelerometer | Posture, Postural Instability, freezing of gate, tremor, dyskinesia, falling, fall potential, On Off medication | Use algorithm to determine if readings are indicative of symptoms combined with other sensors Placed on the users wrist (for tremor mainly but other symptoms besides posture), foot (freezing of gait mainly but other symptoms besides posture), shoulders (posture and other symptoms) front of brace and back (posture and other symptoms). |
| Gyroscope | Posture, Postural Instability, freezing of gate, tremor, dyskinesia, falling, fall potential, On Off medication | Use algorithm to determine if readings are indicative of symptoms combined with other sensors Placed on the users wrist (for tremor mainly but other symptoms besides posture), foot (freezing of gait mainly but other |

-continued

| Sensor | Symptom | How to Monitor |
|---|---|---|
| | | symptoms besides posture), shoulders (posture and other symptoms) front of brace and back (posture and other symptoms). |
| Magnetometer | Posture, Postural Instability, freezing of gate, tremor, dyskinesia, falling, fall potential, On Off medication | Use algorithm to determine if readings are indicative of symptoms combined with other sensors Placed on the users wrist (for tremor mainly but other symptoms besides posture), foot (freezing of gait mainly but other symptoms besides posture), shoulders (posture and other symptoms) front of brace and back (posture and other symptoms). |
| External Inputs (weather, humidity, temp outside, floor plans with GPS) | UV exposure, prediction of symptoms based on external weather | Use algorithm to determine if readings are indicative of symptoms combined with other sensors This would be on the users interface device and would be used as inputs to the algorithm |
| Heart Rate | Postural Instability, freezing of gate, tremor, dyskinesia, falling, fall potential, On Off medication | Use algorithm to determine if readings are indicative of symptoms combined with other sensors Placed on the wrist or in the brace to detect the users heart rate continuously |
| Body Temp | Postural Instability, freezing of gate, tremor, dyskinesia, falling, fall potential, On Off medication | Use algorithm to determine if readings are indicative of symptoms combined with other sensors Under the individuals armpit in the brace to continuously monitor there temperature. |
| Microphone | On Off medication, severity of symptoms, | Use algorithm to determine if readings are indicative of symptoms combined with other sensors |
| EMG | Postural Instability, freezing of gate, tremor, dyskinesia, falling, fall potential, On Off medication | Use algorithm to determine if readings are indicative of symptoms combined with other sensors On the users wrist, arms, legs, foot, stomach, any muscle group that can show symptoms of Parkinson's disease. Continuous monitoring of the user's muscles. |
| EKG | Postural Instability, freezing of gate, tremor, dyskinesia, falling, fall potential, On Off medication | Use algorithm to determine if readings are indicative of symptoms combined with other sensors Located on the user's chest or built into the brace to continuously monitor the users heart |
| EEG | Postural Instability, freezing of gate, tremor, dyskinesia, falling, fall potential, On Off medication | Use algorithm to determine if readings are indicative of symptoms combined with other sensors Located in a headband or cap on the user's head for continuous brain monitoring. |
| GPS | Locational symptoms | Use algorithm to determine if readings are indicative of symptoms combined with other sensors |
| Strain Gauge | Tensioning of brace, posture | Located on the users device and or on the brace. Use algorithm to determine if readings are indicative of symptoms combined with other sensors Located on the brace either on the back, front or in the straps themselves. Allows us to determine the amount the straps are being pulled and derive the posture of the individual. |
| Pressure detection in shoe | Freezing of gait, uneven gait, instability, fall potential | Use algorithm to determine if readings are indicative of symptoms combined with other sensors Placed in the sole of the users shoe for pressure detection and gate derivation |
| Glucose | Fall potential, symptom severity, sleep quality | Use algorithm to determine if readings are indicative of symptoms combined with other sensors Located in the brace, wrists or other location in contact with the users skin. |
| Hydration/ Galvanic skin response | Fall Potential, postural instability, symptom severity, sleep quality | Use algorithm to determine if readings are indicative of symptoms combined with other sensors Located in the brace, wrists or other location in contact with the users skin. |

In embodiments, sensors may be combined with other wearable components that are in communication with the brace, and may provide auditory and/or tactile feedback to a user. For example, a user may be alerted once a targeted tension level is met or when the risk of a fall is high.

In embodiments, components of the brace, and associated with the brace may be powered by electricity. Electric power may be provided by battery. Batteries may be rechargeable, removable and/or non-removable. Charging may be provided by wired and/or wireless charging. Power may be provided by 120 volt, cord/plug combination (e.g., the U.S. domestic standard), or some foreign equivalent means of providing cord/plug power to a device. In another embodiment, power may be provided by a photovoltaic material, such as photovoltaic fabric, cell and/or plurality of photovoltaic cells.

In embodiments, a software application and user interface, or plurality of software applications, may be used to send, receive and store sensor communications. Such software applications may be associated with a processor or plurality of processors. Such processors may be placed within the brace, in association with the brace through physical connection (e.g., cord or wire), in association with the brace remotely (e.g., through wireless communication and/or the Internet), or some other processor-application combination. Such sensor, software and processor combinations in and/or associated with the brace may be used to measure a user's posture (e.g., based on sensor data), the presence, frequency and/or duration of a user's movement, a user's health state (e.g., vital signs of heart rate, blood pressure and the like), provide longitudinal tracking of health state data, or some other type of data. In embodiments, sensors may be placed within a garment, such as a vest, in an array wherein the number of sensors, distance between sensors, location of sensor placement and/or sensor type is selected to detect a specific health state or plurality of health states. For example, IMU sensors may be placed in a vest-type garment in the upper and lower portions in order to detect posture positioning. Additional sensors deployed in regions such as the thigh, shin or elsewhere may further enhance posture detection, and the detection of events such as a slouch, tilt of some other unfavorable position of the user.

In embodiments, the brace and its associated software and processor may transmit and present recommended posture or other data for a user to emulate and/or strive to achieve. Algorithms may be used to determine recommended user posture or other states. Users may be provided graphic or multimedia guidance to a user. For example, as a user changes one's posture, a graphic representation of the current posture may be presented to the user on a smart phone or other mobile device, and the goal state presented in the same graphic depiction to allow the user to see the proximity of their current position relative to a goal. Such presentations may also include brace adjustment recommendations (e.g., tension) to apply to the brace to bring, for example, a user's current posture closer in position to the goal state.

In embodiments, the brace and its associated sensors, software, and processor may be used to detect user symptoms. For example, sensor data may be used as surrogate markers representing the presence of medication side effects. For example, a tremor may be detected, lack of movement, slower respiration, or some other activity associated with a medication side effect. In other embodiments, circulation, sleep patterns, muscle usage or non-usage, and aggregate markers used to infer stress in a patient may be inferred by brace-based measurements. Such data may further be used to assist patients in correcting symptoms (e.g., inactivity, poor posture, and the like). Based at least in part on such measurements, the software associated with the brace may send alerts to a user, physician, caregiver or other interested party to inform them of a measured state (e.g., inactivity) of the brace. Alerts may be in the form of a push notification, email, phone call, text message, or some other communication means. Such alerts may be further associated with an action occurring on the brace, such as adjusting a motor and winch to correct poor posture. Such adjustments may be done remotely by a party, such as a physician. In embodiments, physiotherapeutic devices disclosed herein may include monitoring sensor data derived from sensors affixed to a garment, wherein the garment sensors generate data indicative of a physical state of the garment's user, receiving a transmitted sensor datum from the garment, wherein the transmitted sensor datum is received at a processor remote to the garment, searching a plurality of physical states data stored in a database, detecting at least one physical state associated with the received sensor datum, sending a communication to the user, wherein the communication includes a notice that the at least one physical state was detected and a request for the user to confirm experiencing the detected physical state, and receiving a message from the user confirming that the user is experiencing the detected physical state. In embodiments, the received message may indicate that the user is not experiencing the detected physical state and instead indicate the correct physical state the user is experiencing. In embodiments, the communication may be sent to a mobile phone associated with the user. For example, a user may wear a garment with sensors that are outfitting to detect dyskinesia, such as a tremor. The sensors within the garment detect, record and transmit data regarding the user's bodily movements and other physiological data. This data may be transmitted to a processor that is remote to the garment. For example, the garment may communication with a software application that is operating on a mobile phone that is associated with the user and/or in proximity to the user. The software application may further transmit the sensor data and/or a summary of the sensor data, to the remote processor that may then analyze the received sensor data. Part of this analysis may include analyzing the sensor data for a match, similarity or other association with recorded physical states and/or data associated with physical states that are stored in a database. Upon detecting a match, a communication may be transmitted back to the user, such as to the mobile phone, indicating that the physical state was detected and request that the user confirm that she is experiencing the physical state, such as through a text message, voice message, selection of a menu item presented on the phone screen, or some other means. The user may also be provided a means to indicate that she is not experiencing the detected physical state and instead indicate the physical state currently experienced. The confirmation process may operate in part as a quality check on the data received from a garment. For example, if the user is riding in a vehicle, the detected movement data that is transmitted may not be indicative of the users physical state, such as experiencing a tremor, but instead due to the movement of the vehicle over a rough road or some other environmental condition. Knowing that the sensor data is not related to a physical state of the user may allow for this data to be ignored, purged or other wise flagged a false positive indication of the physical state.

In embodiments, the data derived from the brace may be used to infer and/or detect clinical indications, such as Parkinson's disease, orthostatic hypotension, tremor, bradykinesia, dyskinesia, instability or imbalance of a user, quality of life of a user (e.g., UPDRS Score, movement/non-movement), or some other indication.

In embodiments, the brace may provide heating, cooling, air circulation, vibration, massage, or some other type of comfort enhancement.

In embodiments, the brace may accommodate a plurality of body types, including but not limited to, male, female, adult, pediatric, geriatric, slender, obese, short, tall, or some other anthropomorphic feature.

In embodiments, physiotherapeutic devices, including those disclosed herein may comprise sensors. Sensors may include plethysmography band, to measure the breathing rate of the individual wearing the brace, an accelerometer, for change in an individual's position, a gyroscope, for an individual's orientation to the ground plane, a heart rate monitor, a body temperature monitor, and a microphone. The sensors may be integrated to the CALIBRACE using known cut and sew techniques.

In embodiments the sensors are in electronic communication with a processing facility. The processing facility may be on board the device or remote to the device and accessed wirelessly or via the Internet. The device will also be in electronic communication with memory.

In embodiments, data from the sensors will be stored. The stored recorded data may be analyzed using machine learning algorithms. For example, time-series analysis approaches may be used to find the most appropriate sensory data to detect symptoms and conditions. Based on these findings, symptom detection models will be learned from collected data and used to improve symptom detection. A type of time-series analysis algorithms—Segment-based Support Vector Machines may be used for detecting the occurrences of temporal patterns. Seg-SVMs have many advantages: they can simultaneously localize the temporal segment (the start and end time) in which a symptom event takes place, recognize the symptom type of the event, and discard temporal segments not belonging to any predefined symptoms.

During the training stage, Seg-SVM computes the feature representations of positive temporal segments that overlap with the annotated event (occurrence of a symptom), and negative segments that do not overlap with the event. A Seg-SVM score function will be learned from the positive and negative feature representations such that segments with larger percentage of overlap with the event produce a higher score.

During the testing stage, Seg-SVM automatically searches along the continuous sensory data sequence for the segments that produce the highest score. Those segments are then output as the detected occurrences of the trained symptom. Although Seg-SVM is here described in detail, it should be understood by one skilled in the art that any machine learning technique, application of algorithms, and related techniques are compatible with, and may be used within and/or in association with the brace device and its related facilities and apparatus, including software applications.

The detection accuracies produced for each pair of sensory data and symptom will be determined. The sensory data/symptom pair that produces the highest detection accuracy denotes which type of sensory data is informative for detecting a given symptom. Through this approach, appropriate sensory data to detect each symptom can be identified.

The smart brace and algorithms may incorporate as many symptoms as are recognizable with machine learning techniques. This ability to recognize and provide feedback for multiple symptoms may be incorporated into a system to provide feedback and warnings to the patient and caregiver. Feedback may take multiple forms such as a smartphone app, haptic feedback in the brace itself or some other form of communication to both the caretaker and patient.

The processor will be programmed to use the data from any one of the sensors to determine statuses/symptoms such as mood, the posture of the individual, the stability, bradykinesia symptoms, compliance with the brace (whether it is on or off), freezing of gait, dyskinesia symptoms and falling.

In embodiments, the various adjustable components of the support device may be coupled to a mechanism, such as for tightening or loosening the component, which in turn is coupled to the processor. The process may be programmed to actuate the mechanism based on sensor data and/or the determined status of the individual.

The methods and systems described herein may be deployed in part or in whole through a machine that executes computer software, program codes, and/or instructions on a processor. The processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable transitory and/or non-transitory media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the disclosure. In addition, all the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable transitory and/or non-transitory media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the disclosure. In addition, all the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable transitory and/or non-transitory media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable transitory and/or non-transitory media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

What is claimed is:

1. A posture support device, comprising:
a garment portion providing posture support to a torso and shoulders of an individual, wherein the garment portion comprises:
a first sensor secured thereto and a second sensor secured thereto; and
tensioners distributed in the garment portion to adjust a posture of the individual by applying an adjustable force to the torso and the shoulders;
wherein the first sensor generates data indicative of at least one of movement of the individual, the posture of the individual, and change in position of the individual;
wherein the second sensor generates data indicative of at least one of breathing rate, a heart-related parameter of the individual, and a sound related parameter associated with the individual; and
a processor in electronic communication with the first sensor and the second sensor, programmed to determine a status based on the data from the first sensor and the second sensor, wherein the status is selected from the group consisting of bradykinesia, freezing of gait, and dyskinesia.

2. The device of claim 1 wherein the first sensor is selected from the group consisting of a pressure sensor and an accelerometer and wherein the second sensor is selected from the group consisting of a plethysmography band, a gyroscope, a heart rate monitor, and a microphone.

3. The device of claim 1 wherein the processor is configured to control the adjustment of the tensioners for a posture support adjustment to the garment portion based at least in part on the determined status.

4. The device of claim 3 further comprising an output device in electronic communication with the processor, the output device is further programmed to cause the output device to provide feedback to the individual indicating the determined status of the individual.

5. The device of claim 4 wherein the processor is further programmed to cause the output device to receive feedback from the individual on the determined status.

6. The device of claim 5, wherein the received feedback is used to indicate that the individual is not experiencing the determined status of the individual and the feedback is used to refine a model used by the processor used to determine the status.

7. The device of claim 5, wherein the received feedback is used to confirm the determined status of the individual.

8. The device of claim 4, wherein the feedback is an indication of a risk of a fall.

9. The device of claim 8, wherein the tensioners include at least one shoulder strap and wherein the tensioners are activated to provide the shoulders of the individual with enough tension to maintain an upright position.

10. The device of claim 3 wherein the processor is further programmed to adjust a parameter of the device based on the status of the individual, wherein the parameter is at least one of tightening or loosening the tensioners.

11. The device of claim 1 wherein the first sensor is selected from the group consisting of a pressure sensor and an accelerometer and wherein the second sensor is selected from the group consisting of a plethysmography band, a gyroscope, a heart rate monitor, and a microphone;
wherein the processor is further programmed to adjust a parameter of the device based on the status of the individual, and wherein the parameter is at least one of tightening or loosening the garment portion.

12. A posture support device, comprising:
a garment portion providing posture support to a torso and shoulders of an individual, wherein the garment portion-comprises:
a first sensor secured thereto and a second sensor secured thereto; and
tensioners distributed in the garment portion to adjust a posture of the individual by applying a force to the torso and the shoulders;
wherein the first sensor generates data indicative of at least one of movement of the individual, the posture of the individual and change in position of the individual;
wherein the second sensor generates data indicative of at least one of breathing rate, orientation to the ground plane, a heart-related parameter of the individual, a body temperature of the individual, and a sound related parameter associated with the individual; and
a processor in electronic communication with the first sensor and the second sensor, programmed to determine a status based on the data from the first sensor and the second sensor, wherein the processor is configured to control adjustment of the tensioners for a posture support adjustment to the garment based at least in part on the determined status.

* * * * *

UNITED STATES PATENT AND TRADEMARK OFFICE
CERTIFICATE OF CORRECTION

PATENT NO. : 10,694,996 B2
APPLICATION NO. : 15/840675
DATED : June 30, 2020
INVENTOR(S) : Courtney Denise Williamson et al.

Page 1 of 1

It is certified that error appears in the above-identified patent and that said Letters Patent is hereby corrected as shown below:

In the Specification

In Column 8, Line 7, delete "there" and insert -- their --, therefor.

In Column 14, Line 7, delete "thermaform" and insert -- thermoform --, therefor.

In Column 14, Line 43, delete "Plesmography" and insert -- Plethysmography --, therefor.

In Column 16, Line 5, delete "and or" and insert -- and/or --, therefor.

In Column 18, Line 30, delete "other wise" and insert -- otherwise --, therefor.

In the Claims

In Column 24, Lines 50-51, in Claim 12, delete "portion-comprises:" and insert -- portion comprises: --, therefor.

In Column 24, Line 59, in Claim 12, delete "individual" and insert -- individual, --, therefor.

Signed and Sealed this
Tenth Day of November, 2020

Andrei Iancu
*Director of the United States Patent and Trademark Office*